US012747468B2

(12) United States Patent
Wei et al.

(10) Patent No.: US 12,747,468 B2
(45) Date of Patent: Sep. 29, 2026

(54) DIGITAL MICROFLUIDIC APPARATUS AND DRIVING METHOD THEREFOR

(71) Applicants: Beijing BOE Sensor Technology Co., Ltd., Beijing (CN); BOE Technology Group Co., Ltd., Beijing (CN)

(72) Inventors: Qiuxu Wei, Beijing (CN); Wenliang Yao, Beijing (CN); Yongjia Gao, Beijing (CN); Bolin Fan, Beijing (CN); Yingying Zhao, Beijing (CN); Le Gu, Beijing (CN); Li Yang, Beijing (CN)

(73) Assignees: Beijing BOE Sensor Technology Co., Ltd., Beijing (CN); BOE Technology Group Co., Ltd., Beijing (CN)

( * ) Notice: Subject to any disclaimer, the term of this patent is extended or adjusted under 35 U.S.C. 154(b) by 558 days.

(21) Appl. No.: 18/273,558

(22) PCT Filed: Jul. 21, 2022

(86) PCT No.: PCT/CN2022/107069
§ 371 (c)(1),
(2) Date: Jul. 21, 2023

(87) PCT Pub. No.: WO2023/005796
PCT Pub. Date: Feb. 2, 2023

(65) Prior Publication Data

US 2024/0084369 A1 Mar. 14, 2024

(30) Foreign Application Priority Data

Jul. 28, 2021 (CN) ........................ 202110855985.6

(51) Int. Cl.

| | |
|---|---|
| ***C12Q 1/6844*** | (2018.01) |
| ***B01L 3/00*** | (2006.01) |
| ***B01L 7/00*** | (2006.01) |

(52) U.S. Cl.
CPC ........ *C12Q 1/6844* (2013.01); *B01L 3/50273* (2013.01); *B01L 7/52* (2013.01);
(Continued)

(58) Field of Classification Search
None
See application file for complete search history.

(56) References Cited

U.S. PATENT DOCUMENTS

2015/0168234 A1 6/2015 Murakami
2015/0375229 A1 12/2015 Possinger et al.

FOREIGN PATENT DOCUMENTS

CN 102220228 A 10/2011
CN 102559488 A 7/2012
(Continued)

OTHER PUBLICATIONS

Office Action dated Apr. 3, 2025 for CN2021108559856 and English Translation.
(Continued)

*Primary Examiner* — Matthew D Krcha

(57) ABSTRACT

A digital microfluidic apparatus and a driving method therefor. The digital microfluidic apparatus comprises a digital microfluidic chip (10), a thermal control apparatus (20), and an elastic support apparatus (30). The digital microfluidic chip (10) is provided with a droplet channel (91), and the droplet channel (91) is configured to allow droplets (90) to move therein; the thermal control apparatus (20) is disposed on one side of the digital microfluidic chip (10), and is configured to generate at least two independent and non-interference hot zones in the droplet channel (91), and control the temperature of each hot zone; and the elastic support apparatus (30) is disposed on the side of the thermal control apparatus (20) away from the digital microfluidic chip (10), and is configured to drive the thermal control
(Continued)

apparatus (20) to be pasted on the surface of the digital microfluidic chip (10).

18 Claims, 10 Drawing Sheets

(52) U.S. Cl.
CPC ... *B01L 2200/0642* (2013.01); *B01L 2200/16* (2013.01); *B01L 2300/027* (2013.01); *B01L 2300/0645* (2013.01); *B01L 2300/18* (2013.01); *B01L 2400/0415* (2013.01)

(56) References Cited

FOREIGN PATENT DOCUMENTS

| | | | |
|---|---|---|---|
| CN | 102604824 | A | 7/2012 |
| CN | 202415561 | U | 9/2012 |
| CN | 106861779 | A | 6/2017 |
| CN | 107619781 | A | 1/2018 |
| CN | 108970654 | A | 12/2018 |
| CN | 111235007 | A | 6/2020 |
| CN | 111748466 | A | 10/2020 |
| CN | 112218939 | A | 1/2021 |
| WO | 2015073689 | A1 | 5/2015 |

OTHER PUBLICATIONS

International Search Report for PCT/CN2022/107069 Mailed Oct. 11, 2022.

DIGITAL MICROFLUIDIC APPARATUS AND DRIVING METHOD THEREFOR

CROSS-REFERENCE TO RELATED APPLICATIONS

The present application is a U.S. National Phase Entry of International Application No. PCT/CN2022/107069 having an international filing date of Jul. 21, 2022, which claims the priority to the Chinese Patent Application No. 202110855985.6, filed to the CNIPA on Jul. 28, 2021 and entitled "Digital Microfluidic Apparatus and Driving Method Therefor". The above-identified applications are incorporated herein by reference in their entireties.

TECHNICAL FIELD

The disclosure relates to, but is not limited to, the technical field of chemiluminescence detection, in particular to a digital microfluidic apparatus and a driving method therefor.

BACKGROUND

With development of Micro-Electro-Mechanical Systems (MEMS) technologies, a digital MicroFluidics technology has made a breakthrough in drive and control and other aspects of micro-droplets, and has been widely used in biology, chemistry, pharmaceuticals and other fields depending on its own advantages. The digital microfluidics technology is a new interdisciplinary subject involving chemistry, fluid physics, microelectronics, new materials, biology, and biomedical engineering, and can achieve accurate control and manipulation on tiny droplets. Because of its characteristics of miniaturization and integration, the apparatus using microfluidic technology is usually called digital microfluidic chip, which is an important part of Laboratory on a Chip (LOC) system. Various cells and other samples can be cultured, moved, detected and analyzed in digital microfluidic chip, and various cells and other samples can be cultured, moved, detected and analyzed in microfluidic chip, which has great development potential and wide application prospect.

In recent years, digital microfluidic chips have been gradually applied to Polymerase Chain Reaction (PCR) because of their low sample consumption and high sensitivity.

SUMMARY

The following is a summary of subject matters described herein in detail. The summary is not intended to limit the protection scope of claims.

In one aspect, an exemplary embodiment of the disclosure provides a digital microfluidic apparatus including a digital microfluidic chip, a thermal control apparatus and an elastic support apparatus; the digital microfluidic chip is provided with a droplet channel configured for droplets to move therein; the thermal control apparatus is arranged at a side of the digital microfluidic chip, and is configured to generate at least two thermal zones which are independent and non-interfering in the droplet channel and control temperatures of the thermal zones; the elastic support apparatus is arranged on a side of the thermal control apparatus away from the digital microfluidic chip, and the elastic support apparatus is configured to drive the thermal control apparatus to be attached to a surface of the digital microfluidic chip.

In an exemplary embodiment, the thermal control apparatus includes a support body and at least two thermal control bodies; a side of the support body facing the digital microfluidic chip is provided with at least two grooves, the at least two thermal control bodies are respectively arranged in the at least two grooves, and a minimum distance between adjacent thermal control bodies is 0.1 mm to 4 mm.

In an exemplary embodiment, in a plane parallel to the digital microfluidic chip, a shape of a thermal control body is any one or more of the following: square, rectangular, circular and elliptical; a characteristic length of the thermal control body is more than 3 times a droplet diameter.

In an exemplary embodiment, a thermal control body includes a heat source body and a heat transfer body which are stacked, the heat source body is arranged in a groove and is configured to provide a heat source, and the heat transfer body is arranged on a side of the heat source body close to the digital microfluidic chip and is configured to conduct heat of the heat source body; a sum of thicknesses of the heat source body and the heat transfer body is greater than a depth of the groove.

In an exemplary embodiment, a difference between the sum of thicknesses of the heat source body and the heat transfer body and the depth of the groove is 0.5 mm to 2 mm.

In an exemplary embodiment, the digital microfluidic apparatus further includes a temperature sensor; a side of the support body is provided with at least one first through hole, and the first through hole is run through a side wall of the groove; a side of the heat transfer body is provided with at least one sensor hole, the sensor hole is communicated with the first through hole, and the temperature sensor is plugged in the sensor hole.

In an exemplary embodiment, the heat source body further includes a connector; a side of the support body is provided with at least one second through hole, and the second through hole is run through a side wall of the groove; a side of the heat source body is provided with at least one connection hole, the connection hole is communicated with the second through hole, and the connector is plugged in the connection hole.

In an exemplary embodiment, the elastic support apparatus includes an elastic element and a support frame; the support frame includes a bottom frame, a side frame and a top frame; the bottom frame is a plate-shaped structure, the top frame is a plate-shaped structure with a first opening provided in middle, the side frame is a tubular structure, a first end of the side frame is connected with an outer edge of the bottom frame, a second end of the side frame is connected with an outer edge of the top frame, so that the bottom frame, the side frame and the top frame form a first housing cavity for housing the elastic element and the thermal control apparatus, and the first opening is communicated with the first housing cavity; an end of the elastic element away from the digital microfluidic chip is connected with the bottom frame, an end of the elastic element close to the digital microfluidic chip is connected with the thermal control apparatus, and the elastic element is configured to apply an elastic force on the thermal control apparatus so that the thermal control apparatus extends into the first opening and is attached to the surface of the digital microfluidic chip.

In an exemplary embodiment, the digital microfluidic apparatus further includes a cover frame disposed on a side of the digital microfluidic chip away from the thermal control apparatus; the cover frame includes a front frame and a border frame, wherein the front frame is a plate-shaped structure with a second opening provided in middle, the border frame is a tubular structure, a first end of the border frame is connected with the support frame, and a second end of the border frame is connected with an outer edge of the front frame, so that the front frame, the border frame and the support frame form a second housing cavity for housing the digital microfluidic chip, and the digital microfluidic chip is fixed in the second housing cavity.

In an exemplary embodiment, the elastic element includes 3 to 6 springs having a compression distance of 1 mm to 3 mm.

In an exemplary embodiment, the elastic support apparatus includes an elastic element, a support column, and a support base frame; the support base frame is a plate-shaped structure with a first opening provided in middle, an end of the elastic element away from the digital microfluidic chip is connected with the support column, an end of the elastic element close to the digital microfluidic chip is connected with the thermal control apparatus, and the elastic element is configured to apply an elastic force on the thermal control apparatus so that the thermal control apparatus extends into the first opening and is attached to the surface of the digital microfluidic chip.

In an exemplary embodiment, the digital microfluidic further includes a cover frame disposed on a side of the digital microfluidic chip away from the thermal control apparatus, the cover frame includes a front frame and a border frame, wherein the front frame is a plate-shaped structure with a second opening provided in middle, the border frame is a tubular structure, a first end of the border frame is connected with the support base frame, and a second end of the border frame is connected with an outer edge of the front frame, so that the front frame, the border frame and the support base frame form a second housing cavity for housing the digital microfluidic chip, and the digital microfluidic chip is fixed in the second housing cavity.

In an exemplary embodiment, the digital microfluidic apparatus further includes a calibration sensor and a temperature controller, the temperature controller is connected to a temperature sensor and a calibration sensor, respectively; the calibration sensor is configured to be arranged on the digital microfluidic chip in a calibration stage and collecting the temperatures of the thermal zones; the temperature controller is configured to acquire the temperatures of the thermal zones collected by the calibration sensor in the calibration stage, acquire a calibration value based on the temperatures of the thermal zones, acquire a temperature of a heat transfer body collected by the temperature sensor in a test stage, and control a heating amount of the heat source body based on the temperature of the heat transfer body and the calibration value.

In another aspect, an exemplary embodiment of the present disclosure further provides a digital microfluidic driving method employing the above-described digital microfluidic apparatus, including:

S1, generating respectively a first thermal zone, a second thermal zone and a third thermal zone which are independent and non-interfering on the digital microfluidic chip, wherein the first thermal zone has a first temperature for performing a denaturation act, the second thermal zone has a second temperature for performing an extension act, and the third thermal zone has a third temperature for performing an annealing act; or, generating respectively a first thermal zone and second thermal zone which are independent and non-interfering on the digital microfluidic chip, wherein the first thermal zone has a first temperature for performing a denaturation act, and the second thermal zone has a second temperature for performing an annealing act and an extension act;

S2, performing a polymerase chain reaction cycle, including: moving the droplets to the first thermal zone to denature nucleic acid; moving the droplets to the third thermal zone to combine a primer with a nucleic acid template to form a local double strand; moving the droplets to the second thermal zone to synthesize a nucleic acid strand complementary to the template; or, moving the droplets to the first thermal zone to denature nucleic acid; moving the droplets to the second thermal zone to combine a primer with a nucleic acid template to form a local double strand, and synthesizing a nucleic acid strand complementary to the template; and

S3, repeating a polymerase chain reaction cycle.

In an exemplary embodiment, prior to act S1, the method further includes:

determining whether it is a calibration stage, if it is, performing calibration processing, otherwise, performing act S1;

the calibration processing includes:

providing a calibration sensor in at least one thermal zone of the digital microfluidic chip;

acquiring respectively, by a temperature controller, a temperature of a heat transfer body collected by a temperature sensor and a temperature of a thermal zone collected by the calibration sensor; calculating a difference between the temperature of the heat transfer body and the temperature of the thermal zone, and storing the difference as a calibration value; and removing the calibration sensor from the digital microfluidic chip.

Other aspects may be understood upon reading and understanding the drawings and detailed description.

BRIEF DESCRIPTION OF DRAWINGS

The drawings are intended to provide a further understanding of technical solutions of the present disclosure and form a part of the specification, and are used to explain the technical solutions of the present disclosure together with embodiments of the present disclosure, but do not form limitations on the technical solutions of the present disclosure. Shapes and sizes of various components in the drawings do not reflect actual scales, but are only intended to schematically illustrate contents of the present disclosure.

DESCRIPTION OF REFERENCE SIGNS

Figure 1:
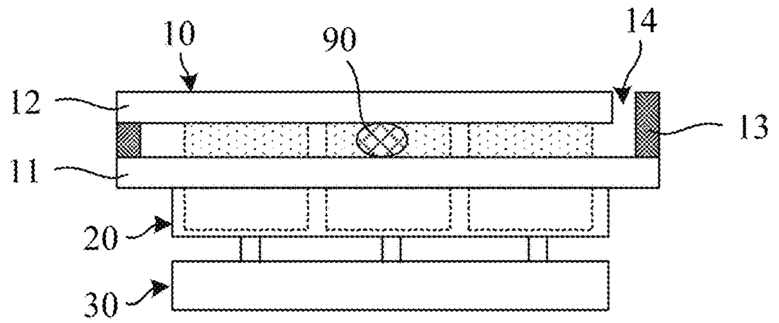
FIG. 1 is a schematic diagram of a structure of a digital microfluidic apparatus according to an exemplary embodiment of the present disclosure.

| | | |
|---|---|---|
| 10-digital microfluidics chip; | 11-first substrate; | 12-second substrate; |
| 13-sealant; | 14-liquid inlet; | 20-thermal control apparatus; |
| 21-support body; | 22-thermal control body; | 23-heat source body; |
| 24-heat transfer body; | 30-elastic support apparatus; | 31-support frame; |
| 32-elastic element; | 33-first opening; | 34-first housing cavity; |
| 35-support column; | 36-support base frame; | 40-cover frame; |
| 41-front frame; | 42-border frame; | 43-second opening; |
| 44-second housing cavity; | 50-temperature sensor; | 51-first thermal zone; |
| 52-second thermal zone; | 53-third thermal zone; | 60-calibration sensor; |
| 70-temperature controller; | 80-input-output apparatus; | 90-droplets; |
| 91-droplet channel; | 100-base frame; | 110-first base substrate; |
| 111-first electrode layer; | 112-first protective layer; | 113-first lyophobic layer; |
| 120-second base substrate; | 121-second electrode layer; | 122-second protective layer; |
| 123-second lyophobic layer; | 210-groove; | 220-first through hole; |
| 230-second through hole; | 231-connection hole; | 232-connector; |
| 241-sensor hole; | 311-bottom frame; | 312-side frame; |
| 313-top frame. | | |

DETAILED DESCRIPTION

To make objectives, technical solutions, and advantages of the present disclosure clearer, the embodiments of the present disclosure will be described in detail with reference to the accompanying drawings. It is to be noted that implementations may be practiced in multiple different forms. Those of ordinary skills in the art may easily understand such a fact that implementations and contents may be transformed into various forms without departing from the purpose and scope of the present disclosure. Therefore, the present disclosure should not be explained as being limited to contents described in following implementation modes only. The embodiments in the present disclosure and features in the embodiments may be combined randomly with each other without conflict.

Scales of the drawings in the present disclosure may be used as a reference in the actual process, but are not limited thereto. The drawings described in the present disclosure are only schematic diagrams of structures, and an implementation of the present disclosure is not limited to shapes or numerical values or the like shown in the drawings.

Ordinal numerals such as “first”, “second”, and “third” in the specification are set to avoid confusion of constituent elements, but not to set a limit in quantity.

In the specification, for convenience, wordings indicating orientation or positional relationships, such as “middle”, “upper”, “lower”, “front”, “back”, “vertical”, “horizontal”, “top”, “bottom”, “inside”, and “outside”, are used for illustrating positional relationships between constituent elements with reference to the drawings, and are merely for facilitating the description of the specification and simplifying the description, rather than indicating or implying that a referred apparatus or element must have a particular orientation and be constructed and operated in the particular orientation. Therefore, they cannot be understood as limitations on the present disclosure. The positional relationships between the constituent elements may be changed as appropriate according to directions for describing the various constituent elements. Therefore, appropriate replacements may be made according to situations without being limited to the wordings described in the specification.

In the specification, unless otherwise specified and defined explicitly, terms “mount”, “mutually connect”, and “connect” should be understood in a broad sense. For example, it may be a fixed connection, or a detachable connection, or an integrated connection. It may be a mechanical connection or an electrical connection. It may be a direct mutual connection, or an indirect connection through middleware, or internal communication between two components. Those of ordinary skills in the art may understand specific meanings of these terms in the present disclosure according to specific situations.

In the specification, “parallel” refers to a state in which an angle formed by two straight lines is above −10° and below 10°, and thus also includes a state in which the angle is above −5° and below 5°. In addition, “perpendicular” refers to a state in which an angle formed by two straight lines is above 80° and below 100°, and thus also includes a state in which the angle is above 85° and below 95°.

Triangle, rectangle, trapezoid, pentagon and hexagon in this specification are not strictly defined, and they may be approximate triangle, rectangle, trapezoid, pentagon or hexagon, etc. There may be some small deformation caused by tolerance, and there may be chamfer, arc edge and deformation, etc.

In the present disclosure, “about” refers to that a boundary is defined not so strictly and numerical values within process and measurement error ranges are allowed.

Digital microfluidic chip is based on the principle of Electrowetting on Dielectric (EWOD), which sets droplets on the surface with hydrophobic layer. With the help of electrowetting effect, the wettability between droplets and lyophobic layer is changed by applying voltage to droplets, resulting in pressure difference and asymmetric deformation inside droplets, and then achieving directional movement of droplets. Digital microfluidics is divided into active digital microfluidics and passive digital microfluidics. A main difference between them is that active digital microfluidics is to drive droplets in an array mode, which may accurately control a droplet at a position to move alone, while passive digital microfluidics is that droplets at all positions are moved or stopped together.

Generally, PCR reaction involves multiple reaction temperatures. For example, PCR reaction may include the following three basic reaction acts: (1) DNA denaturation (90° C. to 96° C.), and hydrogen bonds of double-stranded DNA template are broken under the action of heat to form single-stranded DNA; (2) annealing (60° C. to 65° C.), the system temperature decreases, and primers combines with DNA templates to form local double strands; (3) extension (70° C. to 75° C.), under the action of Taq enzyme (the activity is the best at about 72° C.), dNTP is used as raw material, and starting from the 3' end of primers and extending from 5' to 3' end, the DNA strands complementary to the template are synthesized. After denaturation, annealing and extension, which is a cycle, the DNA content doubles, and most PCR reactions may include 25 to 35 cycles. Research shows that the temperature change rate of cycle switching among various reaction temperatures is very important for the overall PCR reaction efficiency.

According to the research of the inventor of the present application, the existing digital microfluidic apparatus applied to PCR reaction has the problems of slow temperature change rate, large temperature change overshoot, complex structure, large volume and the like. Because the existing digital microfluidic apparatus realizes the cycle switching of reaction temperatures by circulating heating and cooling in a micro-reaction tank, the temperature change rate is slow due to the limitation of heating rate and cooling rate of the temperature change system, and the maximum temperature change rate can only reach 8° C./s. In addition, due to frequent warming and cooling, temperature control needs to introduce temperature overshoot (about 3° C.), which not only takes a long time to regress and stabilize, but also has the risk of affecting enzyme activity. Furthermore, because the variable temperature system adopts semiconductor refrigeration sheet, heat sink, fan and other structures, the apparatus structure is complex, the volume is large, and the cost is high.

In order to solve the problems of slow temperature change rate, large temperature change overshoot, complex structure, large volume and the like existing in the prior digital microfluidic apparatus, an exemplary embodiment of the present disclosure provides a digital microfluidic apparatus. FIG. 1 is a schematic diagram of a structure of a digital microfluidic apparatus according to an exemplary embodiment of the present disclosure. As shown in FIG. 1 the digital microfluidic apparatus may include a digital microfluidic chip 10, a thermal control apparatus 20, and an elastic support apparatus 30. In an exemplary embodiment, the digital microfluidic chip 10 may be provided with a droplet channel configured for droplets 90 to move therein. The thermal control apparatus 20 is disposed on a side of the digital microfluidic chip 10 and is configured to generate at least two thermal zones which are independent and non-interfering in the droplet channel and control a temperature of each thermal zone. The elastic support apparatus 30 is provided on a side of the thermal control apparatus 20 away from the digital microfluidic chip 10 and is configured to drive the thermal control apparatus 20 to be attached to a surface of the digital microfluidic chip 10.

In an exemplary embodiment, the digital microfluidic chip 10 may include a first substrate 11 and a second substrate 12 disposed oppositely, the first substrate 11 and the second substrate 12 may be connected by an sealant 13 such that the first substrate 11, the second substrate 12 and the sealant 13 form a cavity having a suitable gap, and droplets 90 of a polar material (aqueous and/or ionic) are confined in a plane between the first substrate 11 and the second substrate 12. In an exemplary embodiment, multiple spacers may be provided between the first substrate 11 and the second substrate 12 and the multiple spacers may form a droplet channel. In an exemplary embodiment, a drive electrode may be provided on the first substrate 11, and a reference electrode may be provided on the second substrate 12, the drive electrode and the reference electrode are configured to drive the droplets 90 to move in the droplet channel.

In an exemplary embodiment, the digital microfluidic chip 10 may include a liquid inlet 14 configured to input fluid into the droplet channel.

In an exemplary embodiment, the thermal control apparatus 20 may be disposed on a side of the first substrate 11 away from the second substrate 12 and driven by the elastic support apparatus 30 to be press-fitted on the surface of the side. In an exemplary embodiment, the thermal control apparatus 20 may include at least a first thermal control element configured to generate a first thermal zone within a droplet channel of the digital microfluidic chip 10 and control the first thermal zone to have a first temperature, a second thermal control element configured to generate a second thermal zone within the droplet channel of the digital microfluidic chip 10 and control the second thermal zone to have a second temperature, and a third thermal control element configured to generate a third thermal zone within the droplet channel of the digital microfluidic chip 10 and control the third thermal zone to have a third temperature. Three independent and non-interfering thermal zones are formed on the digital microfluidic chip 10, i.e. the three thermal zones on the digital microfluidic chip are created and controlled by the thermal control apparatus.

In an exemplary embodiment, the elastic support apparatus 30 may include a support frame that may be disposed on a side of the thermal control apparatus 20 away from the digital microfluidic chip 10, and an elastic element that may be disposed between the support frame and the thermal control apparatus 20. The elastic element is configured to apply an elastic force to the thermal control apparatus 20 such that the thermal control apparatus 20 is press-fitted to a surface of the digital microfluidic chip 10.

In an exemplary embodiment, the digital microfluidic chip 10 may drive a droplet 90 to move from the first thermal zone to the second thermal zone such that the temperature of the droplet 90 rapidly changes from the first temperature T1 to the second temperature T2, or the digital microfluidic chip 10 may drive the droplet 90 to move from the second thermal zone to the third thermal zone such that the temperature of the droplet 90 rapidly changes from the second temperature T2 to the third temperature T3, a temperature change rate may be greater than or equal to 12° C./s.

In the exemplary embodiments of the present disclosure, the digital microfluidic apparatus in the exemplary embodiments of the present disclosure can be suitable for implementing any on-chip laboratory that requires changing the temperature of a droplet to multiple temperatures as part of a droplet manipulation scheme by providing multiple thermal zones and enabling droplets to move rapidly between the multiple thermal zones.

Figure 2A:
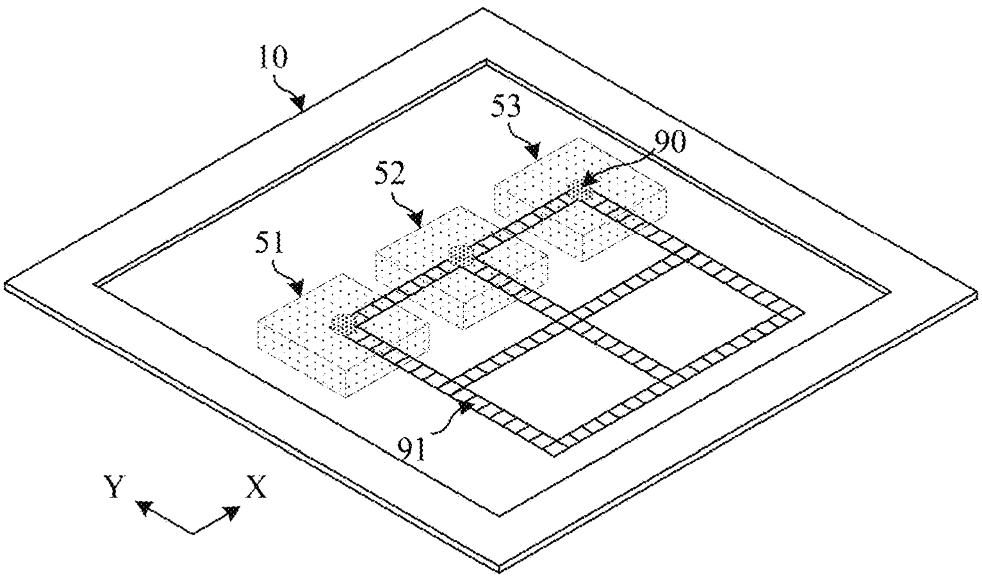
FIGS. 2*a* to 2*c* are schematic diagrams of structures of a digital microfluidic chip according to an embodiment of the present disclosure.
Figure 2B:
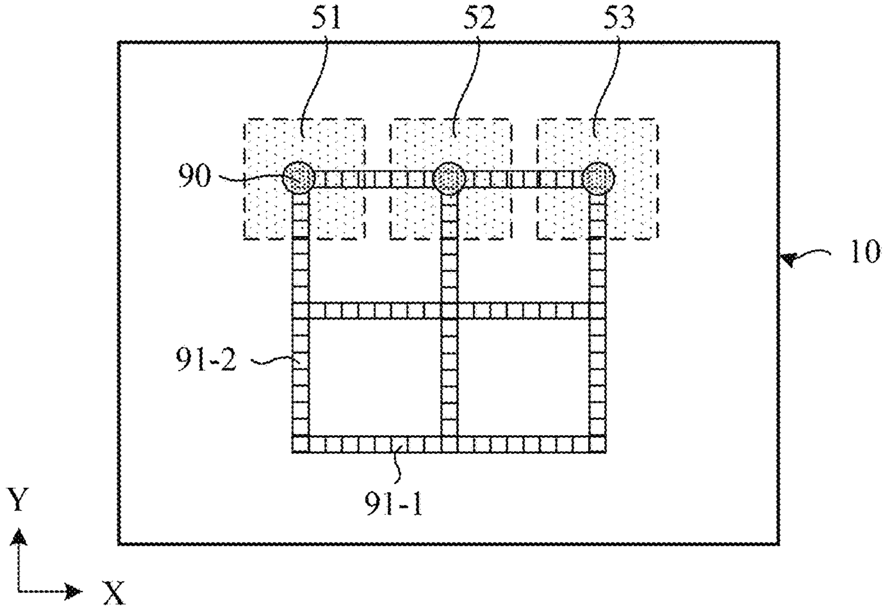
Figure 2C:
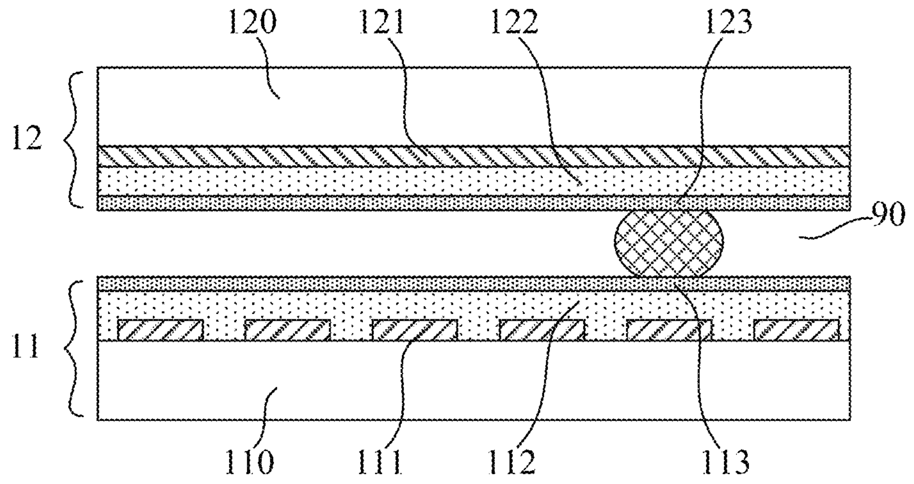

FIGS. 2*a* to 2*c* are schematic diagrams of structures of a digital microfluidic chip according to an exemplary embodiment of the present disclosure. FIG. 2*a* is a schematic three-dimensional diagram of a structure of the digital microfluidic chip, FIG. 2*b* is a schematic planar diagram of a structure of the digital microfluidic chip, and FIG. 2*c* is a schematic sectional diagram of a structure of the digital microfluidic chip. As shown in FIGS. 2*a* and 2*b*, in an exemplary embodiment, a droplet channel 91 is provided on the digital microfluidic chip 10 and the droplet channel 91 is configured for the droplets 90 to move therein. In an exemplary embodiment, the droplet channel 91 may include at least one first channel 91-1 extending along the first direction X and at least one second channel 91-2 extending along the second direction Y, the first channel 91-1 and the second channel 91-2 communicate with each other to form a grid shape, and the first direction X intersects with the second direction Y.

In an exemplary embodiment, a thermal control apparatus located under the digital microfluidic chip 10 forms three independent and non-interfering thermal zones on the droplet channel 91, the three thermal zones are a first thermal zone 51, a second thermal zone 52, and a third thermal zone 53, respectively.

In an exemplary embodiment, the shapes of the three thermal zones may be rectangular on a plane parallel to the digital microfluidic chip.

As shown in FIG. 2*c*, in an exemplary embodiment, the digital microfluidic chip 10 may include a first substrate 11 and a second substrate 12 disposed oppositely. The first substrate 11 may include a first base substrate 110, a first electrode layer 111 disposed on a side of the first base substrate 110 close to the second substrate 12, a first protective layer 112 disposed on a side of the first electrode layer 111 close to the second substrate 12, and a first lyophobic layer 113 disposed on a side of the first protective layer 112 close to the second substrate 12. The second substrate 12 may include a second base substrate 120, a second electrode layer 121 disposed on a side of the second base substrate 120 close to the first substrate 11, a second protective layer 122 disposed on a side of the second electrode layer 121 close to the first substrate 11, and a second lyophobic layer 123 disposed on a side of the second protective layer 122 close to the first substrate 11.

In an exemplary embodiment, the first electrode layer 111 may include multiple first electrodes which are disposed at positions corresponding to the droplet channel at intervals and are configured to drive a droplet to move within the droplet channel. The first electrode layer 111 may be made of metal materials, such as silver (Ag), copper (Cu), aluminum (Al) or molybdenum (Mo), etc., or alloy materials composed of metals, such as aluminum neodymium alloy (AlNd) or molybdenum-niobium alloy (MoNb), etc. The alloy material may be a single-layer structure or a multilayer composite structure, such as a composite structure composed of a Mo layer, a Cu layer, and a Mo layer. The first protective layer 112 covers the first electrode layer 111 and has good insulation property. The material of the first protective layer 112 may be an insulating material, such as resin, polyimide (PI), silicon oxide (SiOx), silicon nitride (SiNx), silicon oxynitride (SiON), or the like, and may be a single-layer structure or a multi-layer composite structure. The first lyophobic layer 113 has good lyophobic property and causes the droplet 90 to have a large surface tension when it is in direct contact with the droplet 90. The contact angle between the droplet 90 and the first lyophobic layer 113 is the initial contact angle. By applying voltage to the corresponding first electrode, the first lyophobic layer 113 at the corresponding position of the first electrode accumulates electric charges, thereby changing the wetting characteristics between the first lyophobic layer 113 and the droplet 90 attached to the surface of the first lyophobic layer 113, thus changing the contact angle between the droplet 90 and the first lyophobic layer 113, thereby deforming the droplet 90 and generating a pressure difference inside the droplet 90, thus achieving the manipulation for the droplet 90. The material of the first lyophobic layer 113 may be a fluoropolymer such as Teflon Perfluororesin (CYTOP) or the like.

In an exemplary embodiment, if the first protective layer 112 has good lyophobic property, the droplet 90 may be provided in direct contact with the first protective layer 112, and the first substrate 11 may include the first base substrate 110, the first electrode layer 111, and the first protective layer 112. If the first lyophobic layer 113 has good insulation property, the first lyophobic layer 113 may be provided to directly cover the first electrode layer 111, and the first substrate 11 may include the first base substrate 110, the first electrode layer 111, and the first lyophobic layer 113, which is not limited in the disclosure.

In an exemplary embodiment, the second electrode layer 121 may include a reference electrode configured to apply a reference potential to provide a reference voltage to multiple first electrodes such that there is a large voltage difference between the first electrode and the reference electrode so that a large driving voltage can be formed to manipulate the droplet 90 to move. In an exemplary embodiment, the reference electrode may be a face electrode, an orthographic projection of the face electrode on the first substrate includes orthographic projections of multiple first electrodes on the first base substrate. In another exemplary embodiment, the reference electrode may be multiple strip electrodes. For example, the strip-shaped reference electrodes may be of strip shape extending along the first direction X, and an orthographic projection of each strip-shaped reference electrode on the first base substrate includes orthographic projections of multiple first electrodes sequentially arranged in the first direction X on the first base substrate. The second electrode layer 121 may be made of metal materials, such as silver (Ag), copper (Cu), aluminum (Al) or molybdenum (Mo), etc., or alloy materials composed of metals, such as aluminum neodymium alloy (AlNd) or molybdenum-niobium alloy (MoNb), etc. The alloy material may be a single-layer structure or a multilayer composite structure, such as a composite structure composed of a Mo layer, a Cu layer, and a Mo layer.

In an exemplary embodiment, the second protective layer 122 covers the second electrode layer 121 with good insulation property, and the material of the second protective layer 122 may be an insulating material such as resin, polyimide (PI), silicon oxide (SiOx), silicon nitride (SiNx), silicon oxynitride (SiON), etc., and may be a single-layer structure, or may be a multi-layer composite structure. The second lyophobic layer 123 has good lyophobic property and causes the droplet 90 to have a large surface tension when it is in direct contact with the droplet 90. The material of the second lyophobic layer 123 may be a fluoropolymer such as Teflon Perfluororesin (CYTOP) or the like.

In an exemplary embodiment, if the second protective layer 122 has good lyophobic property, the droplet 90 may be provided in direct contact with the second protective layer 122, and the second substrate 11 may include the second base substrate 120, the second electrode layer 121, and the second protective layer 122. If the second lyophobic layer 123 has good insulation property, the second lyophobic layer 123 may be provided to directly cover the second electrode layer 121. The second substrate 12 may include the second base substrate 120, the second electrode layer 121, and the second lyophobic layer 123, which is not limited in the disclosure.

In an exemplary embodiment, on a plane parallel to the digital microfluidic chip, the shape of a first electrode may be any one or more of the following: square, rectangular, rhombic, trapezoidal, polygonal, circular and elliptical, and the arrangement of the first electrodes may be any one or more of the following: a straight line arranged along the first direction X or the second direction Y, a cross, a T-shape or an X-shape arranged along the first direction X and the second direction Y, etc., which may be determined according to the function of manipulating droplets, and the present disclosure is not limited thereto.

In an exemplary embodiment, a region outside of the droplet channel 91 on the digital microfluidic chip 10 may include multiple dummy units where corresponding first electrodes and reference electrodes may be provided, but there is no function of manipulating droplets.

In an exemplary embodiment, the digital microfluidic chip 10 may be a single substrate, for example, including only a first substrate or only a second substrate and the present disclosure is not limited thereto.

An exemplary embodiment of the present disclosure provides a digital microfluidic chip that manipulates a droplet based on a dielectric wetting effect, based on a voltage generated by an electrode, in combination with a lyophobic property between a lyophobic layer and a droplet, thereby enabling a droplet to move in a droplet channel.

As shown in FIGS. 2*a* to 2*c*, the first thermal zone 51, the second thermal zone 52 and the third thermal zone 53 may be arranged in sequence along the first direction X. M electrodes may be arranged between a first electrode corresponding to the center point of the first thermal zone 51 and a first electrode corresponding to the center point of the second thermal zone 52, and N electrodes may be arranged between a first electrode corresponding to the center point of the second thermal zone 52 and a first electrode corresponding to the center point of the third thermal zone 53. In exemplary embodiments, M, N may be about 5 to 15. For example, M, N can be about 8. In this way, when a droplet 90 moves from the center point of the first thermal zone 51 to the center point of the second thermal zone 52, the droplet 90 passes through nine first electrodes. In an exemplary embodiment, it takes about 0.2 s for a droplet 90 to pass through one first electrode and about 1.8 s for nine first electrodes. When the temperature difference between the first thermal zone 51 and the second thermal zone 52 is about 23° C., the temperature change rate of the droplet 90 is about 12.8° C./s, which is far greater than the maximum temperature change rate of the existing structure.

In an exemplary embodiment, the first thermal zone, the second thermal zone, and the third thermal zone may be arranged in order of temperature increasing or decreasing to reduce temperature crosstalk between the temperature zones.

In an exemplary embodiment, the first temperature T1 of the first thermal zone may be about 95° C.±1° C., the second temperature T2 of the second thermal zone may be about 72° C.±1° C., and the third temperature T3 of the third thermal zone may be about 60° C.±1° C.

Figure 3:
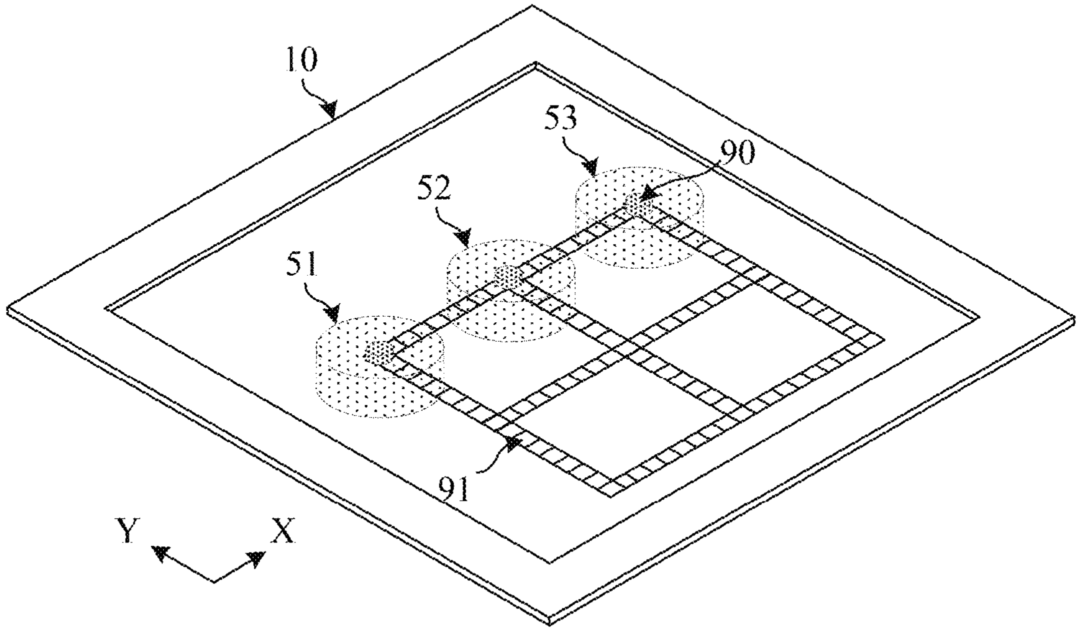
FIG. 3 is a schematic diagram of a structure of another digital microfluidics chip according to an embodiment of the present disclosure.

FIG. 3 is a schematic diagram of a structure of another digital microfluidics chip according to an exemplary embodiment of the present disclosure. In an exemplary embodiment, the structure of the digital microfluidic chip of the present exemplary embodiment is substantially the same as those of the foregoing embodiments, except that the shapes of the three thermal zones may be circular on the plane parallel to the digital microfluidic chip, as shown in FIG. 3.

In an exemplary embodiment, since the three thermal zones on the digital microfluidic chip 10 are created and controlled by the three thermal control elements of the thermal control apparatus 20, the shapes of the thermal zones correspond to the shapes of the thermal control elements. For a square-shaped or rectangular-shaped thermal control element, a thermal zone of the thermal control element formed on the digital microfluidic chip 10 is substantially square-shaped or rectangular-shaped. For a circular or elliptical thermal control element, a thermal zone of the thermal control element formed on the digital microfluidic chip 10 is substantially circular or elliptical.

Figure 4:
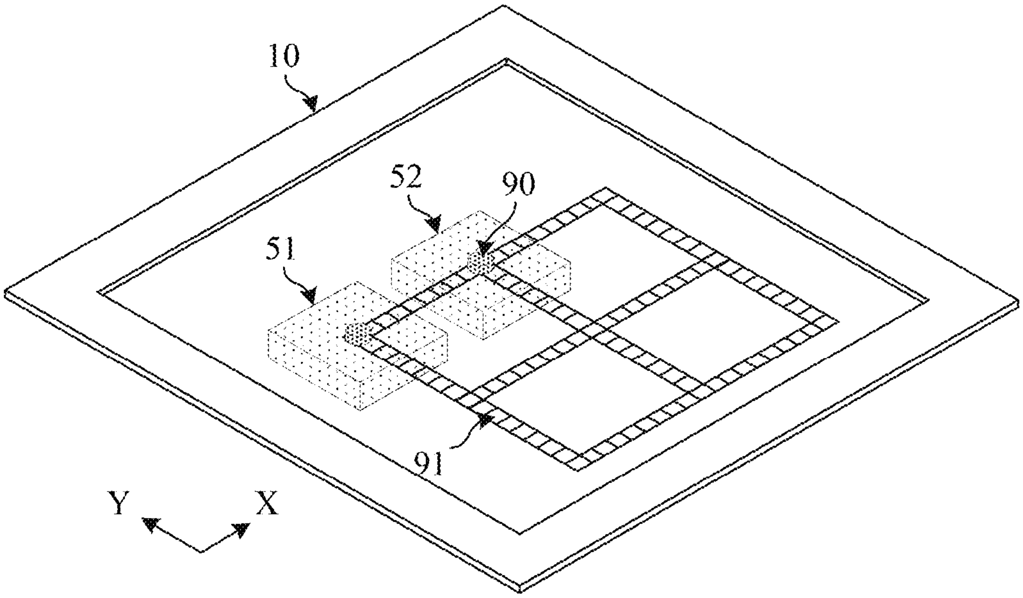
FIG. 4 is a schematic diagram of a structure of another digital microfluidics chip according to an embodiment of the present disclosure.

FIG. 4 is a schematic diagram of a structure of another digital microfluidics chip according to an exemplary embodiment of the present disclosure. In an exemplary embodiment, the structure of the digital microfluidic chip of the present exemplary embodiment is substantially the same as those of the foregoing embodiments, except that two thermal zones are formed on the digital microfluidic chip 10, as shown in FIG. 4.

In an exemplary embodiment, for a digital microfluidic apparatus applied to a PCR reaction, when the needed primer annealing temperature differs from the extension temperature by no more than 3° C., the annealing processing and the extension processing can be performed in a thermal zone, combining annealing and extension into one step (e.g. 60° C.), i.e. a two-step PCR. The two-step PCR method does not need to switch between annealing and extension, so the PCR time can be shortened. At this time, two thermal zones can be formed on the digital microfluidic chip 10, and the droplets can be driven to circulate between the two temperature zones to realize the reaction.

Figure 5:
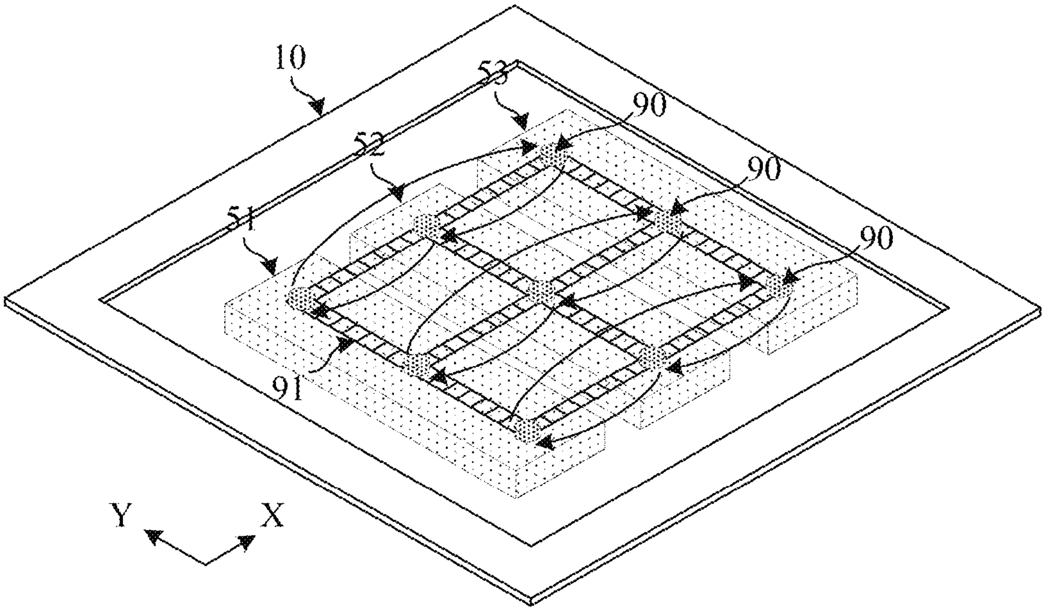
FIG. 5 is a schematic diagram of a structure of another digital microfluidics chip according to an embodiment of the present disclosure.

FIG. 5 is a schematic diagram of a structure of another digital microfluidics chip according to an exemplary embodiment of the present disclosure. In an exemplary embodiment, the structure of the digital microfluidic chip of the present exemplary embodiment is substantially the same as those of the foregoing embodiments, except that three droplet channels 91 for performing biochemical reactions are provided on the digital microfluidic chip, and thermal zones of the same temperature in the three droplet channels 91 are generated by a thermal control element, so that each thermal zone can cover three droplet channels. The droplets 90 in each droplet channel can circulate among three thermal zones according to the corresponding driving timing, and can simultaneously complete multi-channel biochemical reactions, as shown in FIG. 5.

Figure 6A:
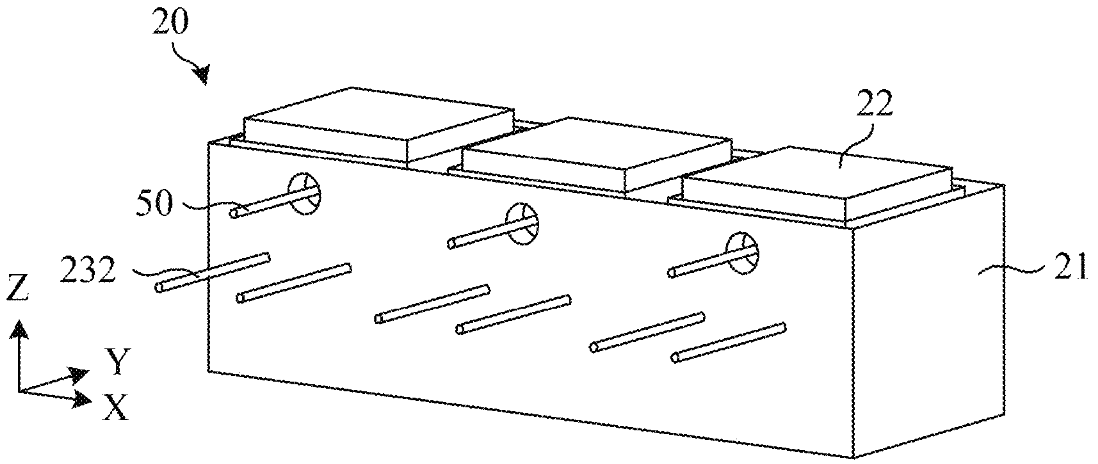
FIGS. 6*a* to 6*b* are schematic diagrams of structures of a thermal control apparatus according to an embodiment of the present disclosure.
Figure 6B:
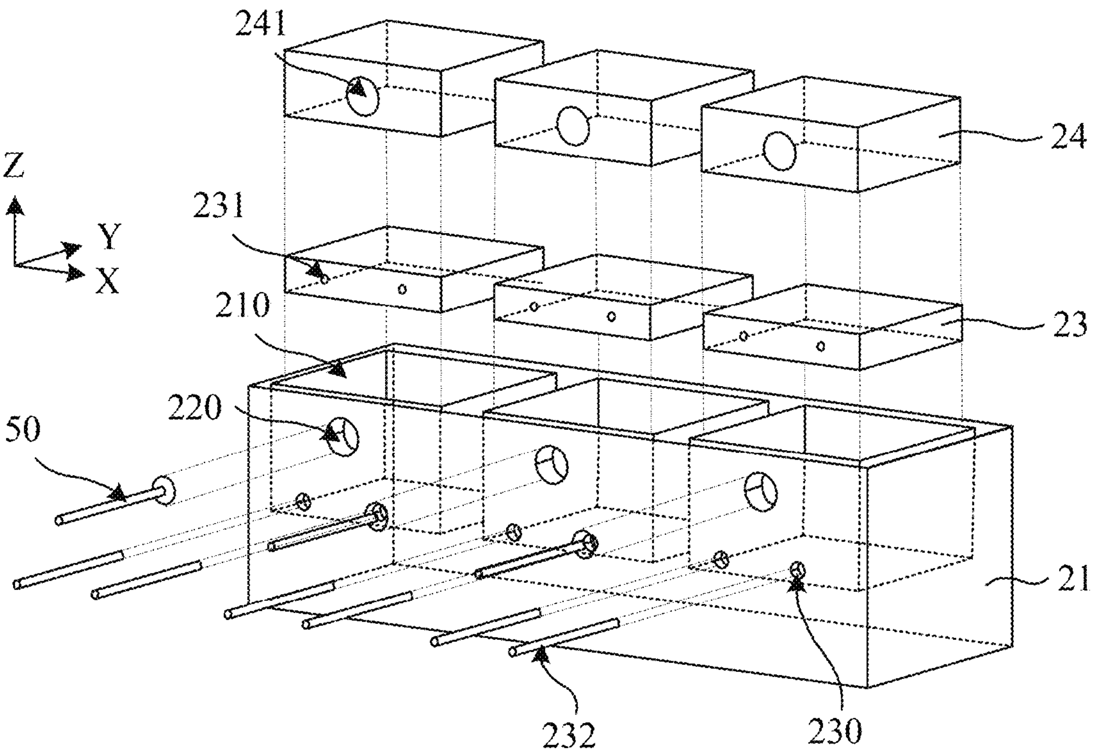

FIGS. 6*a* to 6*b* are schematic diagrams of structures of a thermal control apparatus according to an exemplary embodiment of the present disclosure. FIG. 6*a* is a schematic three-dimensional diagram of a structure of the thermal control apparatus, and FIG. 6*b* is a schematic explosion diagram of the thermal control apparatus. As shown in FIGS. 6*a* and 6*b*, in an exemplary embodiment, the thermal control apparatus 20 may include a support body 21 and multiple thermal control bodies 22, the support body 21 is configured to carry multiple thermal control bodies 22, the multiple thermal control bodies 22 are respectively disposed within the support body 21, and are configured to respectively form multiple thermal zones on the digital microfluidic chip.

In an exemplary embodiment, the support body 21 may be rectangular, and multiple grooves 210 are provided on a side of the support body 21 in the third direction Z (a side facing the digital microfluidic chip), and the multiple grooves 210 are configured to mount, fix, and carry multiple thermal control bodies 22, and the third direction Z may be perpendicular to the plane of the digital microfluidic chip.

In an exemplary embodiment, multiple grooves 210 may be sequentially disposed along the first direction X, and a minimum distance between adjacent grooves 210 may be about 0.1 mm to 4 mm.

In an exemplary embodiment, in a plane parallel to the digital microfluidic chip, the shape of the groove 210 may be any one or more of the following: square, rectangular, circular, and elliptical.

In an exemplary embodiment, for the groove 210 having a square shape, the side length of the groove 210 may be a characteristic length of the groove and may be greater than 3 times the droplet diameter. For a droplet having a diameter of about 3 mm, the side length of the groove 210 may be about 10 mm. For a rectangular groove 210, the long side of the rectangle extends along the first direction X, and the long side of the groove 210 may serve as a characteristic length of the groove, which may be greater than 3 times the droplet diameter. For the groove 210 having a circular shape, the diameter of the groove 210 may be a characteristic length of the groove and may be greater than 3 times the diameter of the droplet. For a groove 210 having an elliptical shape, a long axis of the elliptical shape extends along the first direction X, and the long axis of the groove 210 may serve as a characteristic length of the groove, which may be greater than 3 times the droplet diameter.

In an exemplary embodiment, the support body 21 may be made of a material having good thermal insulation and heat resistance such as bakelite, acrylic, and the like.

In an exemplary embodiment, in a plane parallel to the digital microfluidic chip, the shape of the thermal control body 22 may be substantially the same as the shape of the groove 210 in which it is located, and may be any one or more of the following: square, rectangular, circular, and elliptical.

In an exemplary embodiment, in a plane parallel to the digital microfluidic chip, the size of the thermal control body 22 may be slightly smaller than the size of the groove 210 in which it is located. For the thermal control body 22 having a square shape, the side length of the square can be used as a characteristic length of the thermal control body and can be greater than 3 times the droplet diameter. For a droplet having a diameter of about 3 mm, the side length of the thermal control body 22 may be about 10 mm. For the thermal control body 22 having a rectangular shape, the long side of the rectangular shape extends along the first direction X, and the long side may serve as a characteristic length of the thermal control body, which may be greater than 3 times the droplet diameter. For the thermal control body 22 having a circular shape, the diameter of the circular thermal control body may be used as a characteristic length of the thermal control body and may be greater than 3 times the droplet diameter. For the thermal control body 22 having an elliptical shape, a long axis of the elliptical shape extends along the first direction X, and the long axis may serve as a characteristic length of the thermal control body, which may be greater than 3 times the droplet diameter.

In an exemplary embodiment, the thermal control body 22 having a square planar shape may form a square thermal zone on the digital microfluidic chip, the thermal control body 22 having a rectangular planar shape may form a rectangular thermal zone on the digital microfluidic chip, the thermal control body 22 having a circular planar shape may form a circular thermal zone on the digital microfluidic chip, and the thermal control body 22 having an elliptical planar shape may form an elliptical thermal zone on the digital microfluidic chip. The thermal control body 22 having a circular planar shape has the advantages of having a small contact area with the digital microfluidic chip and not easily affecting reagent reactions in areas other than the thermal zone.

In an exemplary embodiment, each thermal control body 22 may include a heat source body 23 and a heat transfer body which are stacked, the heat source body 23 is disposed in the groove 210 and configured to provide a heat source, and the heat transfer body 24 is disposed on a side of the heat source body 23 in the third direction Z and configured to conduct heat of the heat source body 23, respectively forming multiple thermal zones on the digital microfluidic chip.

In an exemplary embodiment, the sum of the thicknesses of the heat source body 23 and the heat transfer body 24 may be greater than the depth of the groove 210 such that a portion of the heat transfer body 24 protrudes from the groove 210, that is, the surface of the heat transfer body 24 on the side in the third direction X is higher than the surface of the support body 21 on the side in the third direction X. In the present disclosure, the depth of the groove, the thickness of the heat source body and the thickness of the heat transfer body are all dimensions in the third direction Z.

In an exemplary embodiment, the difference between the sum of the thicknesses of the heat source body and the heat transfer body and the depth of the groove may be about 0.5 mm to 2 mm.

In an exemplary embodiment, the material of the heat transfer body 24 may be a material having good thermal conductivity, such as aluminum or copper, etc. The heat transfer body 24 is in direct contact with a surface of a first substrate on the side away from a second substrate in the digital microfluidic chip, and the heat generated by the heat source body 23 is uniformly transferred to the digital microfluidic chip to form a thermal zone on the digital microfluidic chip.

In an exemplary embodiment, at least one first through hole 220 may be provided on a side of the support body 21 in the second direction Y or a side of the support body 21 in a direction opposite to the second direction Y, and the at least one first through hole 220 may be provided in a region where at least one groove 210 is located and is run through the side wall of the groove 210. At least one sensor hole 241 may be provided on a side of the at least one heat transfer body 24 in the second direction Y or a side of the at least one heat transfer body 24 in a direction opposite to the second direction Y, the sensor hole 241 is configured to mount the fixed temperature sensor 50. In an exemplary embodiment, the sensor hole 241 may be a blind hole. After the heat transfer body 24 is disposed in the groove 210, the positions of the first through hole 220 and the sensor hole 241 correspond to each other, and the first through hole 220 is communicated with the sensor hole 241 so that the temperature sensor 50 can be plugged in the sensor hole 241 through the first through hole 220.

In an exemplary embodiment, the temperature sensor 50 is configured to sense the temperature of the heat transfer body 24. The temperature sensor 50 may include a sensor head and a sensor rod, the sensor head may be in a disk shape having temperature sensing elements such as an NTC thermistor, a PTC thermistor, a platinum resistor, a thermocouple, etc. disposed therein, and the sensor head may be disposed at an end of the sensor rod such that the sensor head may extend inside the heat transfer block, such as a central region of the heat transfer block, to sense the temperature inside the heat transfer body 24.

In an exemplary embodiment, after the temperature sensor 50 is plugged in the sensor hole 241, the sensor hole 241 may be filled with silica gel or silicone grease having good thermal conductivity, thereby fixing the temperature sensor 50.

In an exemplary embodiment, at least one second through hole 230 may be provided on a side of the support body 21 in the second direction Y or a side of the support body 21 in a direction opposite to the second direction Y, and the at least one second through hole 230 may be provided in a region where at least one groove 210 is located and is run through the side wall of the groove 210. At least one connection hole 231 may be provided on a side of the at least one heat source body 23 in the second direction Y or a side of the at least one heat source body 23 in a direction opposite to the second direction Y, the connection hole 231 is configured to mount and fix the connector 232. In an exemplary embodiment, the connection hole 231 may be a blind hole. After the heat source body 23 is disposed in the groove 210, the positions of the second through hole 230 and the connection hole 231 correspond to each other, and the second through hole 230 is communicated with the connection hole 231 so that the connector 232 can be plugged in the connection hole 231 through the second through hole 230.

In an exemplary embodiment, the heat source body 23 may be a ceramic heating plate which has the advantages of good thermal conductivity, uniform heating, good heat preservation performance, corrosion resistance, long service life and the like. The connector 232 may be rod-shaped, one end of which is connected to a power source and the other end of which is electrically connected to the heat source body 23 by being plugged in the connection hole 231.

Figure 7:
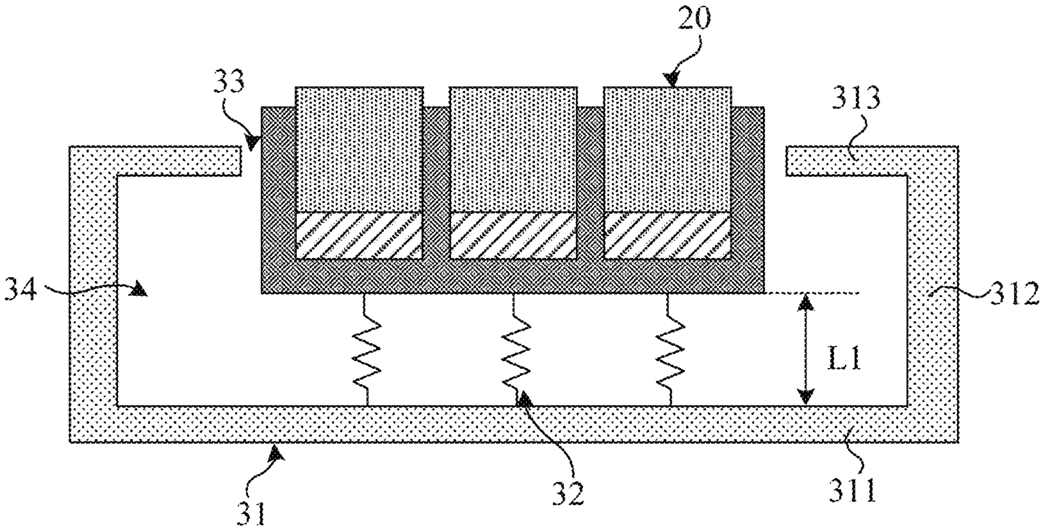
FIG. 7 is a schematic diagram of a structure of an elastic support apparatus according to an embodiment of the present disclosure.

FIG. 7 is a schematic diagram of a structure of an elastic support apparatus according to an exemplary embodiment of the present disclosure. As shown in FIG. 7, in an exemplary embodiment, the elastic support apparatus 30 may include a support frame 31 and an elastic element 32, an end of the elastic element 32 away from the digital microfluidic chip 10 is connected to the support frame 31, and an end of the elastic element 32 close to the digital microfluidic chip 10 is connected to a thermal control apparatus 20, the elastic element 32 is configured to apply an elastic force to the thermal control apparatus 20 such that the thermal control apparatus 20 is attached to a surface of the digital microfluidic chip 10.

In an exemplary embodiment, the support frame 31 may include a bottom frame 311, a side frame 312, and a top frame 313. The bottom frame 311 may have a plate-shaped structure, the top frame 313 may have a plate-shaped structure with a first opening 33 provided in the middle, and the side frame 312 may have a tubular structure. A first end of the side frame 312 is connected to the outer edge of the bottom frame 311, and a second end of the side frame 312 is connected to the outer edge of the top frame 313, so that the bottom frame 311, the side frame 312, and the top frame 313 form a first housing cavity 34 capable of housing the elastic member 32 and the thermal control apparatus 20, and the first opening 33 is communicated with the first housing cavity 34.

In an exemplary embodiment, one end of the elastic element 32 is connected to the bottom frame 311, and the other end of the elastic element 32 is connected to the surface of the thermal control apparatus 20 on the side close to the bottom frame 311. In the thermal control apparatus 20 elastically supported by the elastic element 32, the side close to the elastic element 32 is provided in the first housing cavity 34, and the side away from the elastic element 32 projects from the first opening 33, i.e. the distance between the surface of the thermal control apparatus 20 on the side away from the bottom frame 311 and the bottom frame 311 is greater than the distance between the surface of the top frame 313 on the side away from the bottom frame 311 and the bottom frame 311.

In an exemplary embodiment, the elastic element 32 may be three to six springs which are connected to the bottom frame 311 and the thermal control apparatus 20 respectively.

In an exemplary embodiment, after the thermal control apparatus is connected to multiple springs (i.e. when the digital microfluidic chip is not loaded), the length of the spring is L1.

Figure 8:
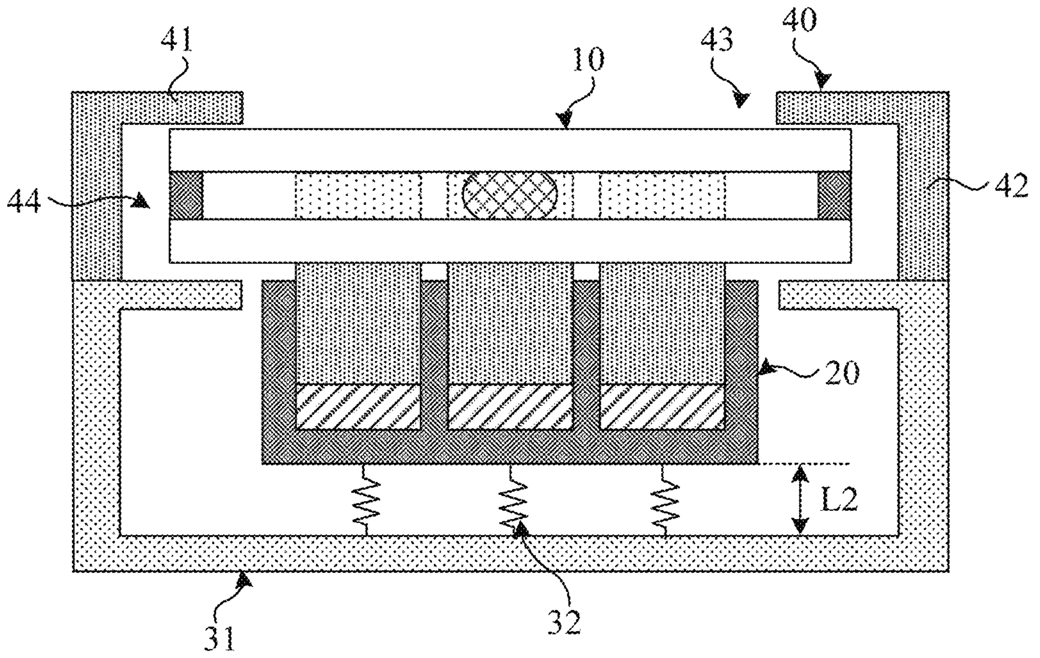
FIG. 8 is a schematic diagram of a structure of a cover plate according to an embodiment of the present disclosure.

FIG. 8 is a schematic diagram of a structure of a cover plate according to an exemplary embodiment of the present disclosure. As shown in FIG. 8, in an exemplary embodiment, the digital microfluidic apparatus may further include a cover frame 40 which may include a front frame 41 and a border frame 42. The front frame 41 may have a plate-shaped structure with a second opening 43 provided in the middle, and the border frame 42 may have a tubular structure. The first end of the border frame 42 is connected with the top frame 313 of the support frame 31, and the second end of the border frame 42 is connected with the outer edge of the front frame 41, so that the front frame 41 and the border frame 42 in the cover frame 40 and the top frame 313 in the support frame 31 form a second housing cavity 44 capable of housing the digital microfluidic chip 10, and the first opening 33 and the second opening 43 are respectively communicated with the second housing cavity 44.

In an exemplary embodiment, the assembly process of the digital microfluidic apparatus of an exemplary embodiment of the present disclosure may include: after connecting the lower side of the thermal control apparatus 20 with the elastic element 32 in the elastic support apparatus 30, arranging the digital microfluidic chip 10 on the upper side of the thermal control apparatus 20, then pressing the front frame 41 of the cover frame 40 on the digital microfluidic chip 10, contacting the border frame 42 of the cover frame 40 with the top frame 313 of the support frame 31 by applying pressure, fixing the cover frame 40 with the support frame 31 by a connector, and fixing the digital microfluidic chip 10 in a second accommodating cavity 44 defined between the cover frame 40 and the support frame 31.

In the process of pressing down, the elastic element 32 is compressed, and the elastic force of the elastic element 32 acts on the thermal control apparatus 20, so that multiple heat transfer bodies 24 of the thermal control apparatus 20 are in close contact with the lower surface of the digital microfluidic chip 10, so that uniform heat transfer can be achieved, and multiple thermal zones can be formed on the digital microfluidic chip 10.

In an exemplary embodiment, a spring is used for the elastic element 32, and the length of the spring is L2 after the cover frame 40 is fixed with the support frame 31 (i.e., after the digital microfluidic chip is loaded). The compression distance L1-L2 of the spring may be set to be about 1 mm to 3 mm, which can not only ensure that the thermal control apparatus 20 is in close contact with the digital microfluidic chip 10, but also ensure that the spring has a certain elastic force, achieving thermal stability and thermal repeatability of multiple crimping.

Figure 9:
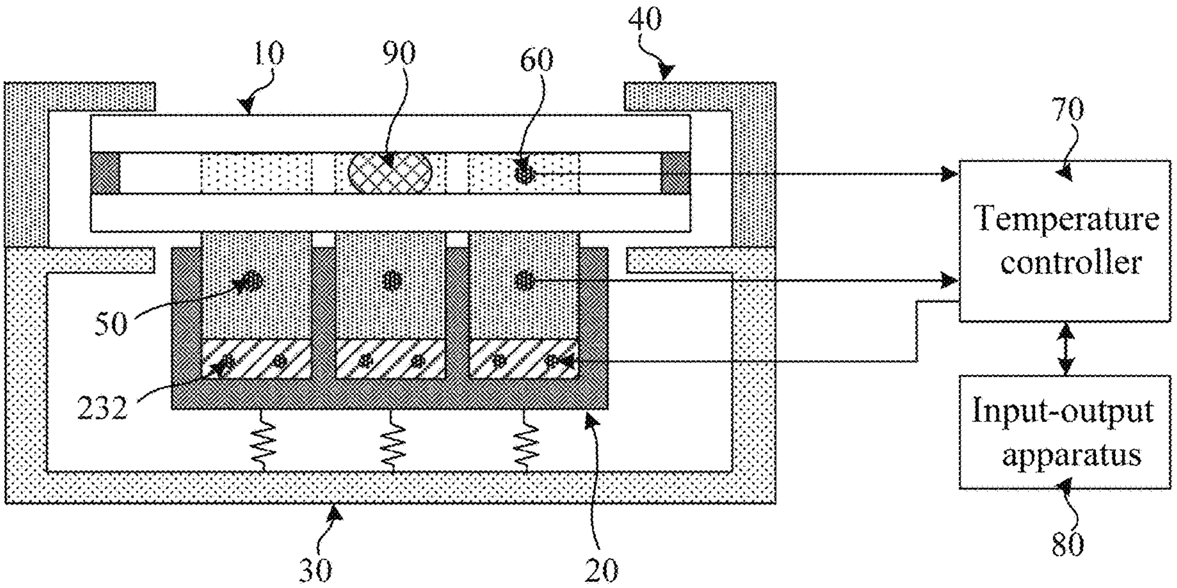
FIG. 9 is a schematic diagram of a structure of another digital microfluidic apparatus according to an embodiment of the present disclosure.

FIG. 9 is a schematic diagram of a structure of another digital microfluidic apparatus according to an exemplary embodiment of the present disclosure. As shown in FIG. 9, in an exemplary embodiment, the digital microfluidic apparatus may include a digital microfluidic chip 10, a thermal control apparatus 20, an elastic support apparatus 30, a cover frame 40, a temperature sensor 50, a calibration sensor 60, a temperature controller 70, and an input-output apparatus 80. The structures of the digital microfluidic chip 10, the thermal control apparatus 20, the elastic support apparatus 30, and the cover frame 40 are substantially the same as those of the foregoing embodiments and will not be described here.

In an exemplary embodiment, the temperature controller 70 is connected to a connector 232 plugged in the heat source body 23, a temperature sensor 50 plugged in the heat transfer body 24, and a calibration sensor 60 disposed inside the digital microfluidic chip 10, respectively. The temperature controller 70 is configured to acquire a calibration value in a calibration stage, acquire a temperature of the heat transfer body collected by the temperature controller 70 in a test stage, and control the heating amount of the heat source body 23 through the connector 232 according to the temperature of the heat transfer body and the calibration value.

In an exemplary embodiment, during the calibration stage, multiple calibration sensors 60 may be disposed inside the digital microfluidic chip 10, and are configured to collect temperatures within the digital microfluidic chip 10, and after the calibration is completed, the calibration sensors 60 are removed from the digital microfluidic chip 10.

In an exemplary embodiment, during the calibration stage, multiple calibration sensors 60 may be respectively disposed at the center of multiple preset thermal zones in the digital microfluidic chip 10, and temperatures of various thermal zones are collected at multiple temperature points. After the temperature controller 70 acquires the temperature of the heat transfer body collected by the temperature sensor 50 and the temperature of the thermal zone collected by the calibration sensor 60, respectively, a difference between the temperature of the heat transfer body and the temperature of the thermal zone can be obtained, which can be used as a calibration value. In the subsequent test stage, the temperature of the heat transfer body collected by the temperature controller 70 minus the calibration value can be used as the temperature value of the thermal zone in the digital microfluidic chip 10.

In an exemplary embodiment, the calibration sensor 60 may employ an NTC thermistor, a PTC thermistor, a platinum resistor, a thermocouple, or the like, and the size of the calibration sensor 60 may be smaller than the cartridge thickness of the digital microfluidic chip 10.

In an exemplary embodiment, in the calibration stage, the temperature controller 70 obtains the temperature of the heat transfer body collected by the temperature sensor 50 and the temperature of the thermal zone collected by the calibration sensor 60, respectively, obtains a difference between the temperature of the heat transfer body and the temperature of the thermal zone at each temperature point, and stores the difference as a calibration value. In the testing stage, the temperature controller 70 controls the working voltage of the heating body and the heating amount of the heat source body according to the collected temperature of the heat transfer body and the calibration value stored in advance, thus achieving the temperature control function.

In an exemplary embodiment, an input-output apparatus 80 is in communication with a temperature controller 70, and the input-output apparatus 80 is configured such that a tester inputs set temperature values of multiple thermal zones in a PCR reaction, transmits the set temperature values to the temperature controller 70, receives relevant parameters such as temperature and voltage from the temperature controller 70 to display in real time.

In an exemplary embodiment, the digital microfluidic apparatus may further include a drive circuit connected to the digital microfluidic chip, the drive circuit is configured to control operation of the digital microfluidic chip through a drive signal.

In an exemplary embodiment, the drive circuit may be provided separately or may be provided in a temperature controller or may be provided in an input-output apparatus, and this is not limited in the present disclosure.

Figure 10A:
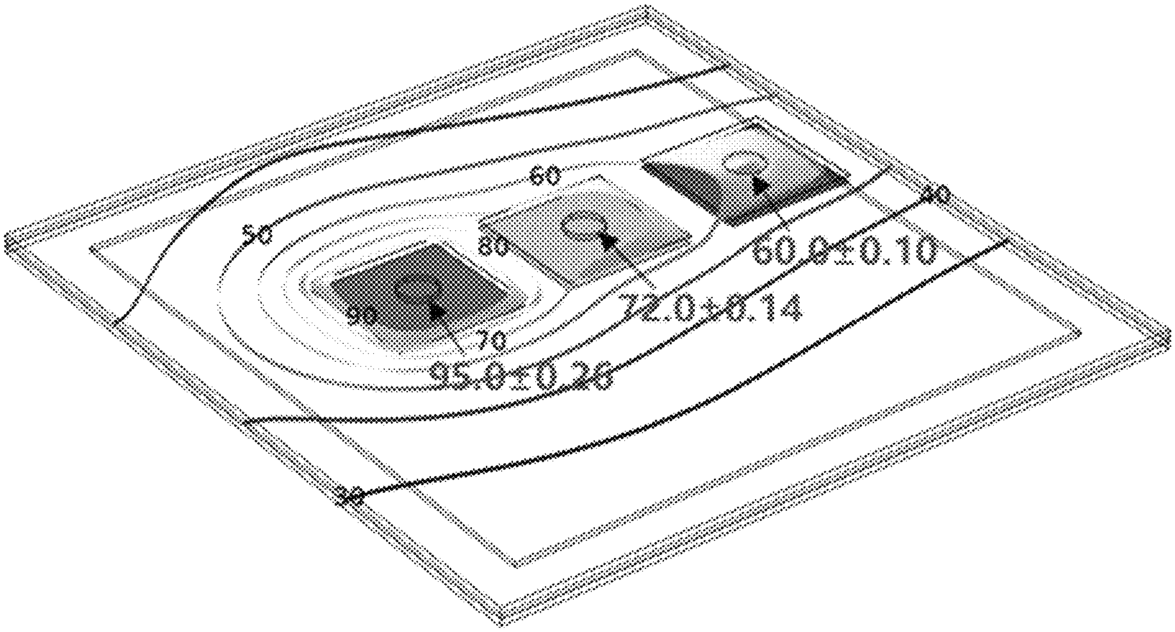
FIGS. 10*a* to 10*c* are schematic diagrams of thermal zone temperature distribution according to an embodiment of the present disclosure.
Figure 10B:
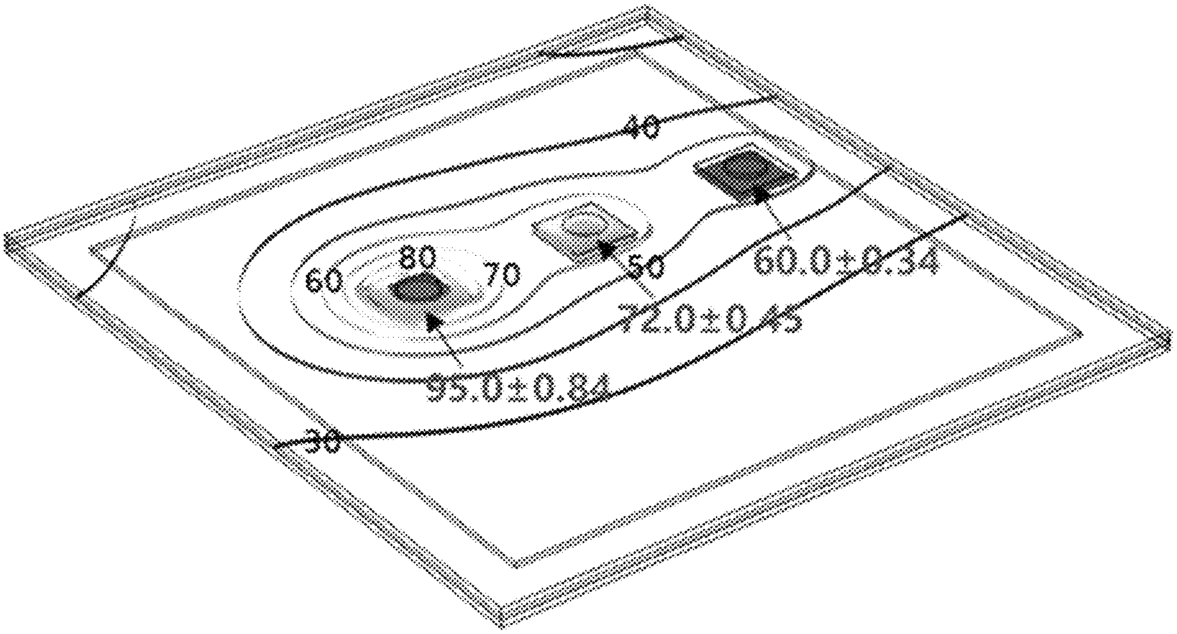
Figure 10C:
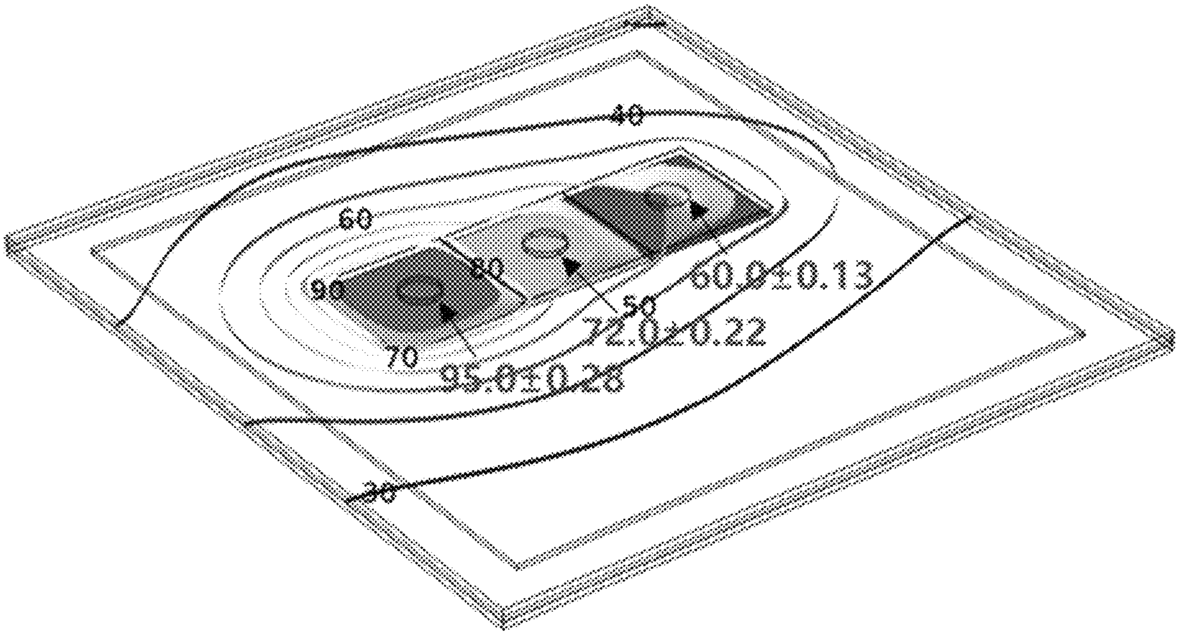

FIGS. 10*a* to 10*c* are schematic diagrams of thermal zone temperature distribution according to an exemplary embodiment of the present disclosure, taking a droplet diameter of about 3 mm as an example. In an exemplary embodiment, simulation analysis shows that the droplet temperature standard deviation σ in the first thermal zone is 0.26° C., the droplet temperature standard deviation σ in the second thermal zone is 0.14° C., the droplet temperature standard deviation σ in the third thermal zone is 0.10° C., and the maximum value of the droplet temperature standard deviations σ in the three thermal zones is 0.26° C. when the side length of the heat transfer block is about 10 mm and the spacing between adjacent thermal control bodies (i.e., the spacing between adjacent heat transfer bodies) is about 3.5 mm, as shown in FIG. 10*a*. According to the principle of triple standard deviation, 3 σ<1° C. Therefore, when the side length of the heat transfer block is about 10 mm and the spacing is about 3.5 mm, the temperatures of droplets in the three thermal zones meet the accuracy requirement of ±1° C. The droplet temperature standard deviation σ is the simulation result of finite element of droplet internal temperature, which is used to represent the difference degree of droplet internal temperature distribution.

In an exemplary embodiment, simulation analysis shows that the droplet temperature standard deviation σ in the first thermal zone is 0.84° C., the droplet temperature standard deviation σ in the second thermal zone is 0.45° C., the droplet temperature standard deviation σ in the third thermal zone is 0.34° C., and the maximum value of the droplet temperature standard deviations σ in the three thermal zones is 0.84° C. when the side length of the heat transfer block is about 5 mm and the spacing between adjacent thermal control bodies (i.e., the spacing between adjacent heat transfer bodies) is about 3.5 mm, as shown in FIG. 10*b*. According to the principle of triple standard deviation, 3 σ>1° C. Therefore, when the side length of the heat transfer block is about 5 mm and the spacing is about 3.5 mm, the temperatures of droplets in the three thermal zones do not meet the accuracy requirement of ±1° C.

In an exemplary embodiment, simulation analysis shows that the droplet temperature standard deviation σ in the first thermal zone is 0.28° C., the droplet temperature standard deviation σ in the second thermal zone is 0.22° C., the droplet temperature standard deviation σ in the third thermal zone is 0.13° C., and the maximum value of the droplet temperature standard deviations σ in the three thermal zones is 0.28° C. when the side length of the heat transfer block is about 10 mm and the spacing between adjacent thermal control bodies (i.e., the spacing between adjacent heat transfer bodies) is about 0.1 mm, as shown in FIG. 10*c*.

According to the principle of triple standard deviation, 3 $\sigma<1°$ C. Therefore, when the side length of the heat transfer block is about 10 mm and the spacing is about 0.1 mm, the temperatures of droplets in the three thermal zones meet the accuracy requirement of ±1° C.

Simulation results show that the smaller the side length of the heat transfer block is, the larger the standard deviation σ of the droplet temperature is, that is, the more uneven the droplet temperature distribution is. When the ratio of the side length of the heat transfer block to the droplet diameter is more than 3 times, the droplet temperatures in the thermal zone meet the accuracy requirement of ±1° C.

Simulation analysis shows that the spacing between adjacent heat transfer bodies has no significant effect on droplet temperature distribution. Therefore, under the premise of machining permission, the spacing between heat transfer blocks can be appropriately reduced to reduce the distance and time consumption of droplets for moving between the thermal zones.

Figure 11:
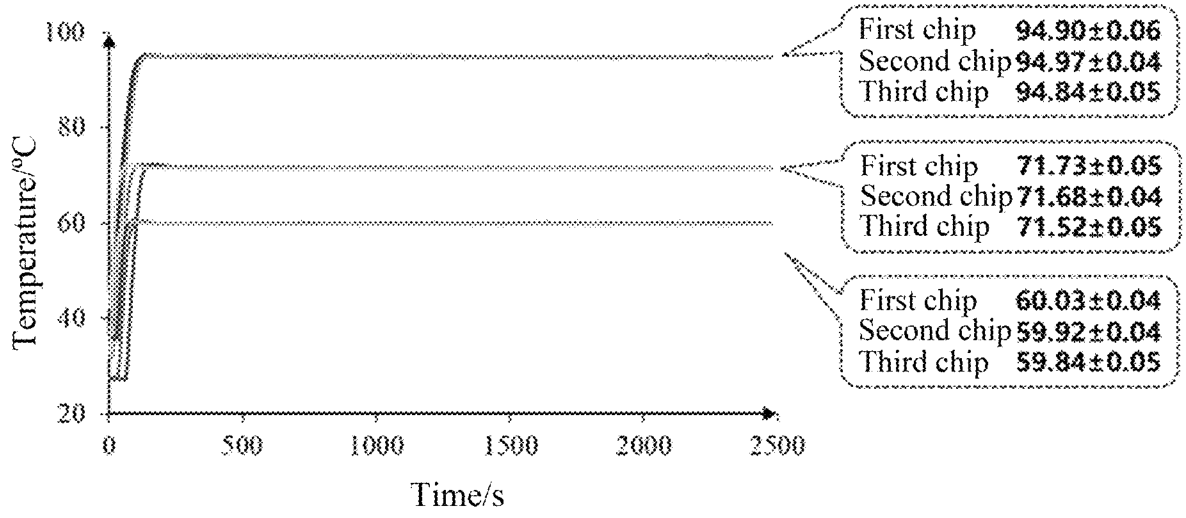
FIG. 11 is a diagram of a thermal zone repeatability test result according to an embodiment of the present disclosure.

FIG. 11 is a diagram of a thermal zone repeatability test result according to an exemplary embodiment of the present disclosure. Three digital microfluidic chips are tested in the same thermal control apparatus and elastic support apparatus. The test result shows that in the entire workflow of the three digital microfluidic chips, the droplet temperature standard deviation is less than or equal to 0.06° C., and the maximum error of droplet temperature is 0.48° C. (target 72° C., measured 71.52° C.), which indicates that the temperature control stability and repeatability of the system are good, as shown in FIG. 11.

Figure 12A:
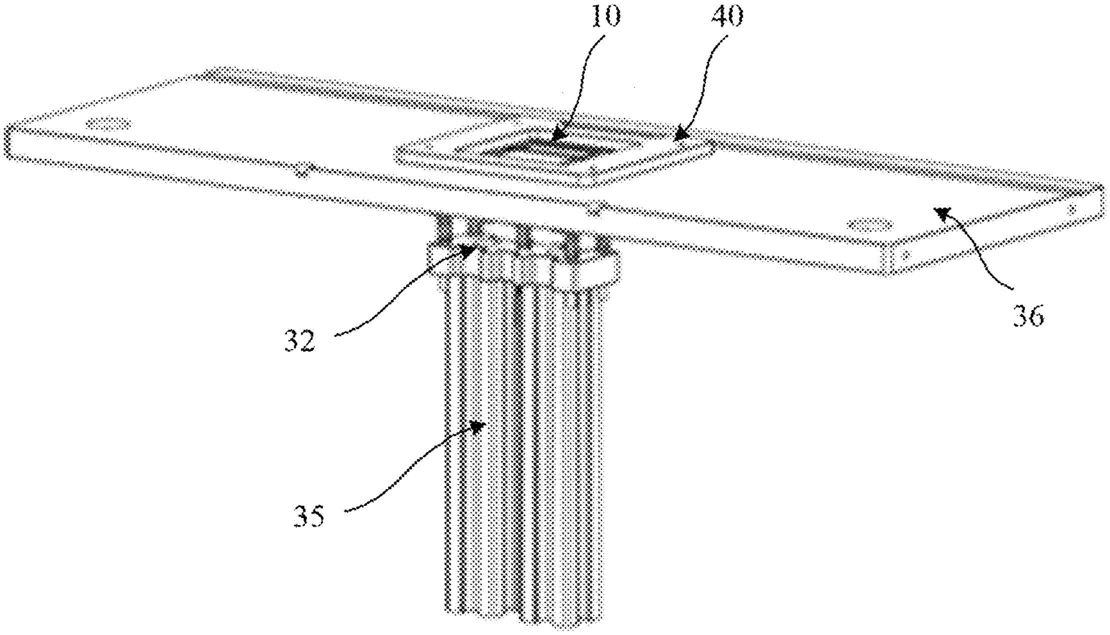
FIGS. 12*a* to 12*b* are schematic diagrams of structures of another elastic support apparatus according to an embodiment of the present disclosure.
Figure 12B:
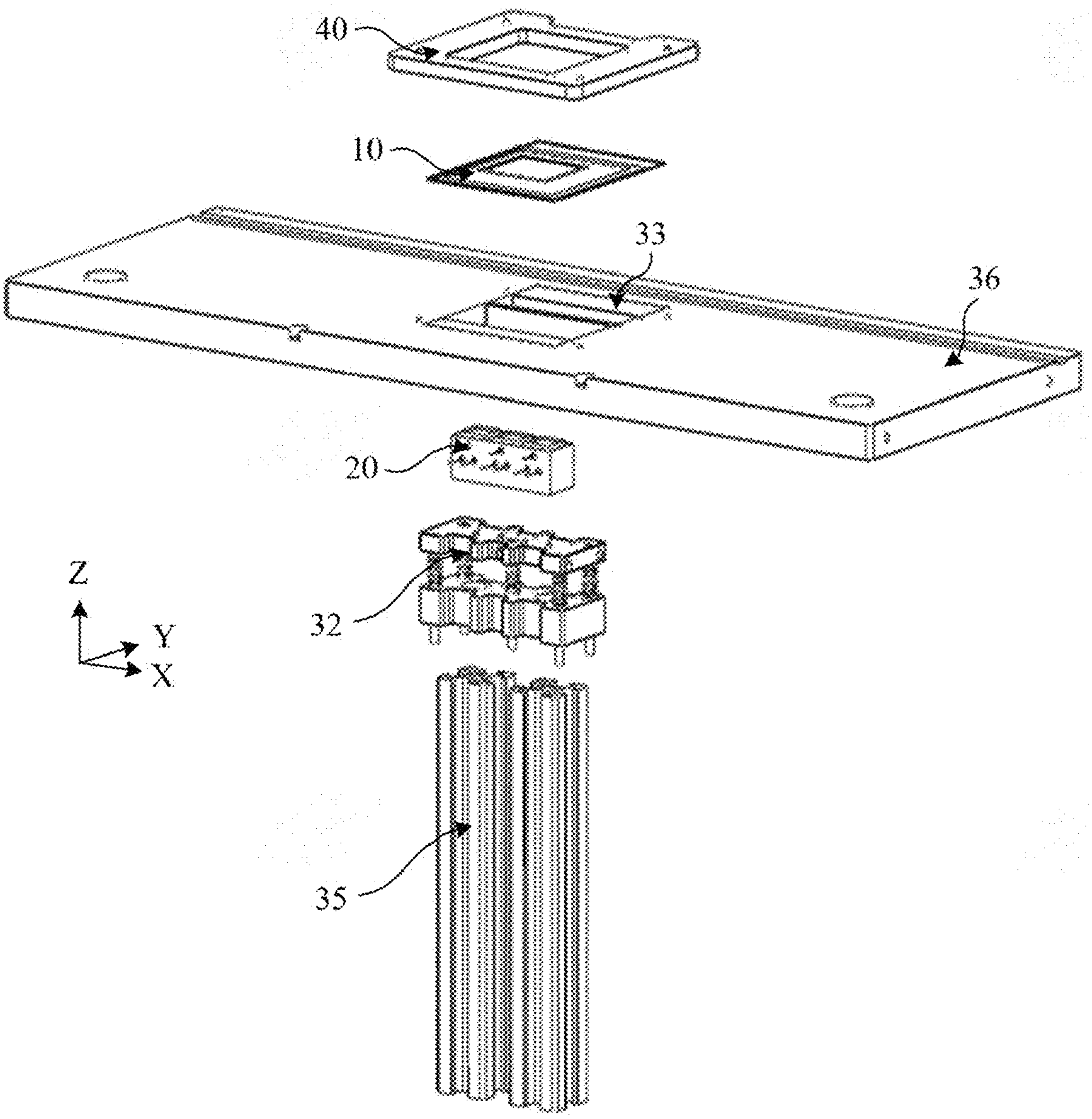

FIGS. 12*a* to 12*b* are schematic diagrams of structures of another elastic support apparatus according to an exemplary embodiment of the present disclosure. FIG. 12*a* is a three-dimensional diagram of a structure of the elastic support apparatus, and FIG. 12*b* is an explosion diagram of the elastic support apparatus. As shown in FIGS. 12*a* to 12*b*, in an exemplary embodiment, the elastic support apparatus 30 may include an elastic element 32, a support column 35, and a support base frame 36. The support base frame 36 may have a plate-shaped structure in which a first opening 33 is provided in the middle, the digital microfluidic chip 10 may be disposed on a side of the support base frame 36 in the third direction Z, and the cover frame 40 may be disposed on a side of the digital microfluidic chip 10 away from the support base frame 36, and the cover frame 40 is connected to the support base frame 36 through multiple screws to fix the digital microfluidic chip 10 between the cover frame 40 and the support base frame 36. An elastic element 32 and a support column 35 may be disposed on a side of the support base frame 36 away from the digital microfluidic chip 10, an end of the elastic element 32 away from the digital microfluidic chip 10 is connected to the support column 35, an end of the elastic element 32 close to the digital microfluidic chip 10 is connected to the thermal control apparatus 20, and the elastic element 32 is configured to apply an elastic force to the thermal control apparatus 20 so that the thermal control apparatus 20 extends into the first opening 33 on the support base frame 36 and is tightly attached to the surface of the digital microfluidic chip 10.

In an exemplary embodiment, the elastic element 32 may be a spring mechanism that may include a bottom plate configured to be connected to an end of the support column 35 on a side close to the digital microfluidic chip 10, a top plate configured to be connected to a surface of the thermal control apparatus 20 on the side away from the digital microfluidic chip 10, and three to six springs disposed between the bottom plate and the top plate and connected to the bottom plate and the top plate respectively.

In an exemplary embodiment, the support column 35 may have a columnar structure connected to the base plate of the elastic element 32 by means of a jack or the like.

Figure 13:
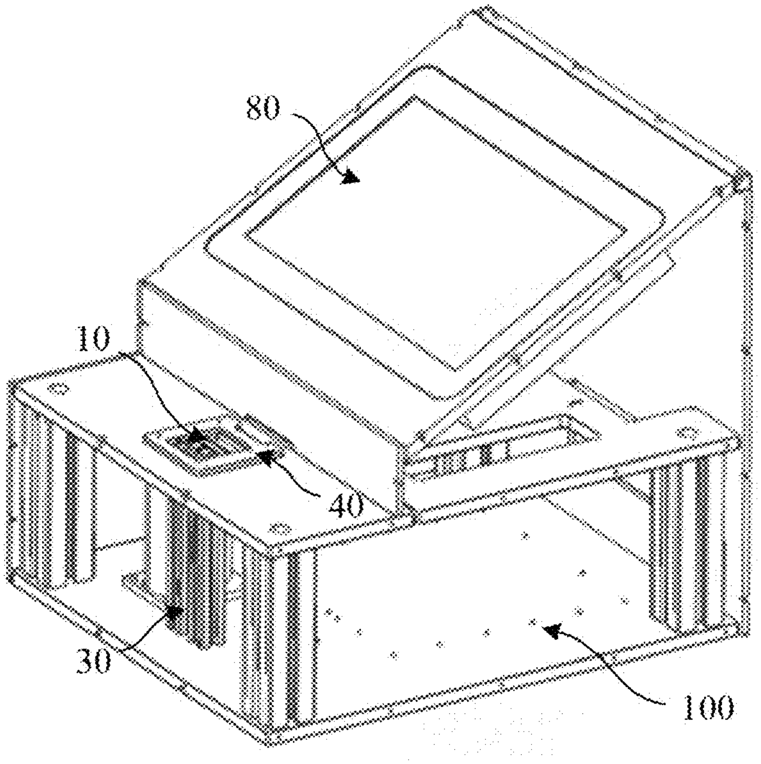
FIG. 13 is a schematic three-dimensional diagram of a structure of another digital microfluidic apparatus according to an embodiment of the present disclosure.

FIG. 13 is a schematic three-dimensional diagram of a structure of another digital microfluidic apparatus according to an exemplary embodiment of the present disclosure. As shown in FIG. 13, the digital microfluidic apparatus may include a digital microfluidic chip 10, a thermal control apparatus, an elastic support apparatus 30, a cover frame 40, a temperature controller, an input-output apparatus 80, and a base frame 100. The structures of the digital microfluidic chip 10, the thermal control apparatus, the elastic support apparatus 30, and the cover frame 40 are substantially the same as those shown in FIGS. 12*a* to 12*b*, and will not be described here.

In an exemplary embodiment, the base frame 100 may include an underframe and a fixing column, the underframe may be of a plate-shaped structure, the fixing column may be of a columnar structure, one end of the fixing column is connected to the underframe, and the other end of the fixing column is connected to the support base frame 36 of the elastic support apparatus 30, so that the elastic support apparatus 30 is fixed to the underframe by the fixing column, and an end of the support column 35 in the elastic support apparatus 30 away from the digital microfluidic chip 10 may be disposed against the underframe.

In an exemplary embodiment, the input-output apparatus 80 may include a touch display through which a tester can input the PCR response and view the result of the PCR response.

Figure 14:
FIG. 14 is a schematic diagram of an appearance of a digital microfluidic apparatus according to an embodiment of the present disclosure.

FIG. 14 is a schematic diagram of an appearance of a digital microfluidic apparatus according to an exemplary embodiment of the present disclosure. As shown in FIG. 14, the digital microfluidic apparatus may include a housing, a thermal control apparatus, an elastic support apparatus, a cover frame, a base frame and other structures are arranged in the housing, and a digital microfluidic chip and an input-output apparatus are arranged on the housing, which has the advantages such as simple appearance, small volume and convenient operation.

As can be seen from the structure of the digital microfluidic apparatus disclosed in the present disclosure, by forming multiple independent and non-interfering thermal zones on the digital microfluidic chip, the droplets circulate and reciprocate in the multiple thermal zones, thus achieving the rapid temperature change of the droplets, and the temperature change rate is fast. For example, when the droplet moves from the second thermal zone with a constant temperature of 72° C. to the first thermal zone with a constant temperature of 95° C., it takes 1.8 s for the droplet to pass through nine first electrodes, and the temperature change rate is 12.8° C./s, which is far greater than the maximum temperature change rate of the existing structure. The digital microfluidic apparatus provided by the disclosure does not need to frequently control the temperature rise and fall of the heating element, so that the temperature change rate can be greatly improved and the temperature change time can be greatly shortened. The digital microfluidic apparatus provided by the disclosure does not need to adopt temperature overshoot, which not only shortens the temperature stabilization time further, but also avoids the influence of temperature overshoot on enzyme activity. Since each thermal zone of the disclosure does not need frequent heating and cooling, a natural cooling scheme can be adopted, thereby avoiding the adoption of forced cooling elements such as semiconductor refrigeration sheets, heat sinks, fans, etc., reducing the structural complexity to the maximum extent, simplifying the structure to the maximum extent, and having the advantages of simple structure, small volume, low cost, etc.

Exemplary embodiments of the present disclosure also provide a method for driving a digital microfluidic apparatus employing the aforementioned digital microfluidic apparatus. In an exemplary embodiment, a method for driving a digital microfluidic apparatus may include:

S1, generating respectively a first thermal zone, a second thermal zone and a third thermal zone which are independent and non-interfering on the digital microfluidic chip, wherein the first thermal zone has a first temperature for performing a denaturation act, the second thermal zone has a second temperature for performing an extension act, and the third thermal zone has a third temperature for performing an annealing act;

S2, performing a polymerase chain reaction cycle, including: moving the droplets to the first thermal zone to denature the nucleic acid; moving the droplets to the third thermal zone to combine the primer with the nucleic acid template to form a local double strand; moving the droplets to the second thermal zone to synthesize a nucleic acid strand complementary to the template;

S3, repeating the polymerase chain reaction cycle.

In an exemplary embodiment, the first temperature T1 of the first thermal zone may be about 95° C.±1° C., the second temperature T2 of the second thermal zone may be about 72° C.±1° C., and the third temperature T3 of the third thermal zone may be about 60° C.±1° C.

In an exemplary embodiment, the first thermal zone, the second thermal zone, and the third thermal zone may be arranged in order of temperature increasing or decreasing to reduce temperature crosstalk between the temperature zones.

In an exemplary embodiment, a determination processing may also be included before act S1. In an exemplary embodiment, the determination processing may include:

determining whether it is a calibration stage, if it is, performing calibration processing, otherwise, performing act S1.

In an exemplary embodiment, the calibration processing may include:

providing a calibration sensor in at least one thermal zone of the digital microfluidic chip;

acquiring respectively, by the temperature controller, the temperature of the heat transfer body collected by the temperature sensor and the temperature of the thermal zone collected by the calibration sensor; calculating a difference between the temperature of the heat transfer body and the temperature of the thermal zone, and storing the difference as a calibration value; and removing the calibration sensor from the digital microfluidic chip.

In an exemplary embodiment, a first calibration sensor may be disposed at a central position of a preset first thermal zone in the digital microfluidic chip, a second calibration sensor may be disposed at a central position of a preset second thermal zone in the digital microfluidic chip, and a third calibration sensor may be disposed at a central position of a preset third thermal zone in the digital microfluidic chip to collect temperatures of various thermal zones as accurately as possible.

In an exemplary embodiment, a thermal control apparatus is provided with a first thermal control body configured to form the first thermal zone, a second thermal control body configured to form the second thermal zone, and a third thermal control body configured to form the third thermal zone, respectively, at positions corresponding to preset first, second and third thermal zones in the digital microfluidic chip. The heat transfer body in the first thermal control body is provided with a first temperature sensor for collecting the temperature of the heat transfer body, the heat transfer body in the second thermal control body is provided with a second temperature sensor for collecting the temperature of the heat transfer body, and the heat transfer body in the third thermal control body is provided with a third temperature sensor for collecting the temperature of the heat transfer body.

In an exemplary embodiment, a temperature controller is connected to the first calibration sensor, the second calibration sensor, the third calibration sensor, the first temperature sensor, the second temperature sensor, and the third temperature sensor, respectively, to obtain temperatures of three heat transfer bodies collected by the three temperature sensors and temperatures of three thermal zones collected by the three calibration sensors, respectively. The temperature controller obtains a calibration value of the first thermal zone based on the temperatures collected by the first calibration sensor and the first temperature sensor, obtains a calibration value of the second thermal zone based on the temperatures collected by the second calibration sensor and the second temperature sensor, and obtains a calibration value of the third thermal zone based on the temperatures collected by the third calibration sensor and the third temperature sensor.

Taking the set temperature value of the first thermal zone as TC as an example, the specific process of calibration processing may include: (1) The temperature controller controls the heat source body in the first heat control body to heat, and obtains in real time the temperature value of the heat transfer body collected by the first temperature sensor and the temperature value of the thermal zone collected by the first calibration sensor. (2) When the temperature value of the thermal zone collected by the first calibration sensor is TC, the temperature value TW of the heat transfer body collected by the first temperature sensor is recorded; (3) The calibration value is calculated, where the calibration value TX=TW-TC. (4) The calibration value TX is stored. In an exemplary embodiment, calibration processing of multiple temperature points can be performed, calibration values of the multiple temperature points can be obtained, and the set temperature values and the calibration values of the multiple temperature points can be fitted to obtain a relationship between the two. For example, taking linear fitting as an example, $y=ax+b$, where x is the set temperature value, y is the calibration value, and a and b are the fitting temperature coefficients obtained by calibration. In this way, the calibration values at other temperature points can be obtained.

In an exemplary embodiment, taking the generation of a first thermal zone on a digital microfluidic chip as an example, act S1 may include:

setting a set temperature value TC1 of the first thermal zone; calculating the target temperature value TW1 of the heat transfer body according to the calibration value, TW1=TC1+TX; controlling, by the temperature controller, the heat source body in the first thermal control body to heat, obtaining the temperature value of the heat transfer body collected by the first temperature sensor in real time, controlling the working voltage according to the collected temperature value of the heat transfer body and the target temperature value TW1, and stopping heating when the collected temperature value of the heat transfer body is equal to the target temperature value TW1.

In an exemplary embodiment, act S2 may include a pre-processing stage and a processing stage, wherein the pre-processing stage may include that the digital microfluidic chip drives the droplets to move to the first thermal zone, maintains the first thermal zone at 95° C. for 3 min, completes DNA pre-denaturation, and then the digital microfluidic chip drives the droplets out of the first thermal zone.

In an exemplary embodiment, the processing stage may include that a digital microfluidic chip drives the droplets to move to a first thermal zone for 0.5 min at the first thermal zone of 95° C. to complete DNA denaturation, then, the digital microfluidic chip drives the droplets to move to the third thermal zone, and maintains the droplets in the third thermal zone at 60° C. for 0.5 min to complete annealing, and then, the digital microfluidic chip drives the droplets to move to the second thermal zone, and maintains the droplets in the second thermal zone at 72° C. for 0.5 min to complete the extension.

In an exemplary embodiment, the repeated execution of the polymerase chain reaction cycle in act S3 is a repeated execution of the processing stage, and the number of cycles may be about 25 to 35.

In an exemplary embodiment, the temperature of the thermal zone, the duration, and the number of cycles and the like may vary according to the reagent type, the length of the DNA fragment, and the like, and the present disclosure is not limited thereto.

Exemplary embodiments of the present disclosure also provide another method for driving a digital microfluidic apparatus employing the aforementioned digital microfluidic apparatus. In an exemplary embodiment, the method for driving a digital microfluidic apparatus may include:

generating respectively a first thermal zone and a second thermal zone which are independent and non-interfering on the digital microfluidic chip, wherein the first thermal zone has a first temperature for performing a denaturation act, and the second thermal zone has a second temperature for performing an annealing act and an extension act;

performing a polymerase chain reaction cycle, including: moving the droplets to the first thermal zone to denature nucleic acid; moving the droplets to the second thermal zone to combine a primer with a nucleic acid template to form a local double strand, and synthesizing a nucleic acid strand complementary to the template; and repeating a polymerase chain reaction cycle.

It can be seen from the driving process of the digital microfluidic apparatus in the disclosure that the disclosure can not only achieve the rapid temperature change of the droplets, but also has a faster temperature change rate, which is far greater than the maximum temperature change rate of the existing structure by adopting the mode of circulating and reciprocating the droplets in multiple thermal ranges. The digital microfluidic apparatus provided by the disclosure does not need to frequently control the temperature rise and fall of the heating element, so that the temperature change rate can be greatly improved and the temperature change time length can be greatly shortened. In addition, the digital microfluidic apparatus provided by the disclosure does not need to adopt temperature overshoot, which not only further shortens the temperature stabilization time length, but also avoids the influence of temperature overshoot on enzyme activity. In addition, since each thermal zone of the disclosure does not need frequent heating and cooling, a natural cooling scheme can be adopted, thereby avoiding the adoption of forced cooling elements such as semiconductor refrigeration sheets, heat sinks, fans, etc., reducing the structural complexity to the maximum extent, simplifying the structure to the maximum extent, and having the advantages of simple structure, small volume, low cost, etc.

Although the implementation modes disclosed in the present disclosure are as above, the described contents are only implementation modes used for convenience of understanding the present disclosure, but are not intended to limit the present disclosure. Any skilled in the art to which the present disclosure pertains, without departing from the spirit and scope disclosed in the present disclosure, may make any modifications and changes in a form and details of implementation. However, the scope of patent protection of the present application should still be subject to the scope defined by the appended claims.

The invention claimed is:

1. A digital microfluidic apparatus, comprising a digital microfluidic chip, a thermal control apparatus and an elastic support apparatus; wherein the digital microfluidic chip is provided with a droplet channel, the droplet channel is configured for droplets to move therein; the thermal control apparatus is provided at a side of the digital microfluidic chip, and is configured to generate at least two thermal zones which are independent and non-interfering in the droplet channel and control temperatures of the thermal zones; the elastic support apparatus is provided on a side of the thermal control apparatus away from the digital microfluidic chip, and the elastic support apparatus is configured to drive the thermal control apparatus to be attached to a surface of the digital microfluidic chip, wherein the thermal control apparatus comprises a support body and at least two thermal control bodies; a side of the support body facing the digital microfluidic chip is provided with at least two grooves, the at least two thermal control bodies are provided respectively in the at least two grooves, each thermal control body comprises a heat source body and a heat transfer body which are stacked, the heat source body is provided in a groove and is configured to provide a heat source, and the heat transfer body is provided on a side of the heat source body close to the digital microfluidic chip and is configured to conduct heat of the heat source body; a sum of thicknesses of the heat source body and the heat transfer body is greater than a depth of the groove;

the at least two thermal zones which are independent and non-interfering comprise a first thermal zone, a second thermal zone and a third thermal zone, the first thermal zone, the second thermal zone, and the third thermal zone are arranged in order of temperature increasing or decreasing; the digital microfluidic chip comprises multiple first electrodes which are disposed at positions corresponding to the droplet channel at intervals and are configured to drive a droplet to move within the droplet channel, M electrodes are arranged between a first electrode corresponding to a center point of the first thermal zone and a first electrode corresponding to a center point of the second thermal zone, and N electrodes are arranged between the first electrode corresponding to the center point of the second thermal zone and a first electrode corresponding to a center point of the third thermal zone, M, N each is 5 to 15.

2. The digital microfluidic apparatus according to claim 1, wherein a minimum distance between adjacent thermal control bodies is 0.1 mm to 4 mm.

3. The digital microfluidic apparatus according to claim 2, wherein the digital microfluidic apparatus further comprises a calibration sensor and a temperature controller, the temperature controller is connected to a temperature sensor and the calibration sensor, respectively; the calibration sensor is configured to be provided on the digital microfluidic chip in a calibration stage and collecting the temperatures of the thermal zones; the temperature controller is configured to acquire the temperatures of the thermal zones collected by the calibration sensor in the calibration stage, acquire a calibration value based on the temperatures of the thermal zones, acquire a temperature of the heat transfer body collected by the temperature sensor in a test stage, and control a heating amount of the heat source body based on the temperature of the heat transfer body and the calibration value.

4. The digital microfluidic apparatus according to claim 2, wherein in a plane parallel to the digital microfluidic chip, a shape of a thermal control body is any one or more of the following: square, rectangular, circular or elliptical; a characteristic length of the thermal control body is more than 3 times a droplet diameter.

5. The digital microfluidic apparatus according to claim 4, wherein the digital microfluidic apparatus further comprises a calibration sensor and a temperature controller, the temperature controller is connected to a temperature sensor and the calibration sensor, respectively; the calibration sensor is configured to be provided on the digital microfluidic chip in a calibration stage and collecting the temperatures of the thermal zones; the temperature controller is configured to acquire the temperatures of the thermal zones collected by the calibration sensor in the calibration stage, acquire a calibration value based on the temperatures of the thermal zones, acquire a temperature of the heat transfer body collected by the temperature sensor in a test stage, and control a heating amount of the heat source body based on the temperature of the heat transfer body and the calibration value.

6. The digital microfluidic apparatus according to claim 1, wherein a difference between the sum of thicknesses of the heat source body and the heat transfer body and the depth of the groove is 0.5 mm to 2 mm.

7. The digital microfluidic apparatus according to claim 6, wherein the digital microfluidic further comprises a calibration sensor and a temperature controller, the temperature controller is connected to a temperature sensor and the calibration sensor, respectively; the calibration sensor is configured to be provided on the digital microfluidic chip in a calibration stage and collecting the temperatures of the thermal zones; the temperature controller is configured to acquire the temperatures of the thermal zones collected by the calibration sensor in the calibration stage, acquire a calibration value based on the temperatures of the thermal zones, acquire a temperature of the heat transfer body collected by the temperature sensor in a test stage, and control a heating amount of the heat source body based on the temperature of the heat transfer body and the calibration value.

8. The digital microfluidic apparatus according to claim 1, wherein the digital microfluidic apparatus further comprises a temperature sensor; a side of the support body is provided with at least one first through hole, and the first through hole is run through a side wall of the groove; a side of the heat transfer body is provided with at least one sensor hole, the sensor hole is communicated with the first through hole, and the temperature sensor is plugged in the sensor hole.

9. The digital microfluidic apparatus according to claim 8, wherein the digital microfluidic apparatus further comprises a calibration sensor and a temperature controller, the temperature controller is connected to a temperature sensor and the calibration sensor, respectively; the calibration sensor is configured to be provided on the digital microfluidic chip in a calibration stage and collecting the temperatures of the thermal zones; the temperature controller is configured to acquire the temperatures of the thermal zones collected by the calibration sensor in the calibration stage, acquire a calibration value based on the temperatures of the thermal zones, acquire a temperature of the heat transfer body collected by the temperature sensor in a test stage, and control a heating amount of the heat source body based on the temperature of the heat transfer body and the calibration value.

10. The digital microfluidic apparatus according to claim 1, wherein the heat source body further comprises a connector; a side of the support body is provided with at least one second through hole, and the second through hole is run through a side wall of the groove; a side of the heat source body is provided with at least one connection hole, the connection hole is communicated with the second through hole, and the connector is plugged in the connection hole.

11. The digital microfluidic apparatus according to claim 1, wherein the elastic support apparatus comprises an elastic element and a support frame; the support frame comprises a bottom frame, a side frame and a top frame; the bottom frame is a plate-shaped structure, the top frame is a plate-shaped structure with a first opening provided in middle, the side frame is a tubular structure, a first end of the side frame is connected with an outer edge of the bottom frame, a second end of the side frame is connected with an outer edge of the top frame, to cause the bottom frame, the side frame and the top frame to form a first housing cavity for housing the elastic element and the thermal control apparatus, the first opening is communicated with the first housing cavity; an end of the elastic element away from the digital microfluidic chip is connected with the bottom frame, an end of the elastic element close to the digital microfluidic chip is connected with the thermal control apparatus, and the elastic element is configured to apply an elastic force on the thermal control apparatus to cause the thermal control apparatus to extend into the first opening and to be attached to the surface of the digital microfluidic chip.

12. The digital microfluidic apparatus according to claim 11, wherein the digital microfluidic apparatus further comprises a cover frame disposed on a side of the digital microfluidic chip away from the thermal control apparatus; the cover frame comprises a front frame and a border frame, wherein the front frame is a plate-shaped structure with a second opening provided in middle, the border frame is a tubular structure, a first end of the border frame is connected with the support frame, and a second end of the border frame is connected with an outer edge of the front frame, to cause the front frame, the border frame and the support frame to form a second housing cavity for housing the digital microfluidic chip, the digital microfluidic chip is fixed in the second housing cavity.

13. The digital microfluidic apparatus according to claim 11, wherein the elastic element comprises 3 to 6 springs having a compression distance of 1 mm to 3 mm.

14. The digital microfluidic apparatus according to claim 1, wherein the elastic support apparatus comprises an elastic element, a support column, and a support base frame; the support base frame is a plate-shaped structure with a first opening provided in middle, an end of the elastic element away from the digital microfluidic chip is connected with the support column, an end of the elastic element close to the digital microfluidic chip is connected with the thermal control apparatus, and the elastic element is configured to apply an elastic force on the thermal control apparatus to cause the thermal control apparatus to extend into the first opening and to be attached to the surface of the digital microfluidic chip.

15. The digital microfluidic apparatus according to claim 14, wherein the digital microfluidic apparatus further comprises a cover frame disposed on a side of the digital microfluidic chip away from the thermal control apparatus, the cover frame comprises a front frame and a border frame, wherein the front frame is a plate-shaped structure with a second opening provided in middle, the border frame is a tubular structure, a first end of the border frame is connected with the support base frame, and a second end of the border frame is connected with an outer edge of the front frame, to cause the front frame, the border frame and the support base frame to form a second housing cavity for housing the digital microfluidic chip, the digital microfluidic chip is fixed in the second housing cavity.

16. The digital microfluidic apparatus according to claim 1, wherein the digital microfluidic apparatus further comprises a calibration sensor and a temperature controller, the temperature controller is connected to a temperature sensor and the calibration sensor, respectively; the calibration sensor is configured to be provided on the digital microfluidic chip in a calibration stage and collecting the temperatures of the thermal zones; the temperature controller is configured to acquire the temperatures of the thermal zones collected by the calibration sensor in the calibration stage, acquire a calibration value based on the temperatures of the thermal zones, acquire a temperature of the heat transfer body collected by the temperature sensor in a test stage, and control a heating amount of the heat source body based on the temperature of the heat transfer body and the calibration value.

17. A digital microfluidic driving method employing the digital microfluidic apparatus according to claim 1, comprising:

S1, generating respectively the first thermal zone, the second thermal zone and the third thermal zone which are independent and non-interfering on the digital microfluidic chip, wherein the first thermal zone has a first temperature for performing a denaturation act, the second thermal zone has a second temperature for performing an extension act, and the third thermal zone has a third temperature for performing an annealing act;

S2, performing a polymerase chain reaction cycle, comprising: moving the droplets to the first thermal zone to denature nucleic acid; moving the droplets to the third thermal zone to combine a primer with a nucleic acid template to form a local double strand; moving the droplets to the second thermal zone to synthesize a nucleic acid strand complementary to the template; and S3, repeating a polymerase chain reaction cycle.

18. The method according to claim 17, wherein prior to act S1, the method further comprises:

determining whether it is a calibration stage, if it is, performing calibration processing, otherwise, performing act S1;

wherein the calibration processing comprises:

providing a calibration sensor in at least one thermal zone of the digital microfluidic chip;

acquiring respectively, by a temperature controller, a temperature of the heat transfer body collected by a temperature sensor and a temperature of a thermal zone collected by the calibration sensor; calculating a difference between the temperature of the heat transfer body and the temperature of the thermal zone, and storing the difference as a calibration value; and removing the calibration sensor from the digital microfluidic chip.

* * * * *